United States Patent [19]

Bras et al.

[11] Patent Number: 5,731,340

[45] Date of Patent: Mar. 24, 1998

[54] GLYCINAMIDE DERIVATIVES, PROCESSES FOR THEIR PREPARATION AND MEDICINES CONTAINING THEM

[75] Inventors: Jean-Pierre Bras; Paul de Cointet, both of Toulouse; Pierre Despeyroux, Labarthe/Leze; Daniel Frehel, allé de Barcelone; Danielle Gully, Muret Toulouse; Jean-Pierre Maffrand, Portet/Garonne; Eric Bignon, Pinsaguel, all of France

[73] Assignee: Sanofi, Paris, France

[21] Appl. No.: 515,640

[22] Filed: Aug. 16, 1995

[30] Foreign Application Priority Data

Aug. 19, 1994 [FR] France ................... 94 10165

[51] Int. Cl.$^6$ ............ A61K 31/40; A61K 31/445; A61K 31/535; C07D 209/42
[52] U.S. Cl. ................ 514/415; 514/235.2; 514/323; 544/143; 546/201
[58] Field of Search ............ 548/492; 546/201; 514/323, 235.2, 415; 544/143

[56] References Cited

U.S. PATENT DOCUMENTS 5,475,106 12/1995 Bourzat ................... 544/58.4

FOREIGN PATENT DOCUMENTS 4243496 3/1994 Germany .
3294253 12/1991 Japan .
WO9113874 9/1991 WIPO .

OTHER PUBLICATIONS

Journal of Medicinal Chemistry, vol. 37, No. 5, Mar. 4, 1994, Washington US, pp. 630–635, M. Holladay, et al, "Tetrapeptide . . . ".

Primary Examiner—C. Warren Ivy
Assistant Examiner—Evelyn Huang
Attorney, Agent, or Firm—Jacobson, Price, Holman & Stern, PLLC

[57] ABSTRACT

The present invention relates to compounds of formula:

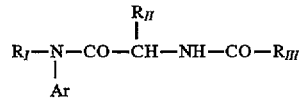

which are agonists of cholecystokinin receptors and pharmaceutical compositions containing them.

10 Claims, No Drawings

GLYCINAMIDE DERIVATIVES, PROCESSES FOR THEIR PREPARATION AND MEDICINES CONTAINING THEM

The present invention relates to glycinamide derivatives, to a process for their preparation and to the medicines containing them.

More particularly, the subject of the present invention is new non-peptide agonists of cholecystokinin (CCK) receptors.

CCK is a peptide which, in response to food ingestion, is secreted at the peripheral level and participates in the control of many digestive processes (Crawley J. N. et al., Peptides, 1994, 15 (4), 731–735).

CCK was subsequently identified in the brain and could be the comonest neuropeptide acting as neuromodulator of cerebral functions by stimulation of receptors of CCK-B type (Crawley J. N. et al., Peptides, 1994, 15 (4), 731–735). CCK interacts in the central nervous system with the neuronal transmission mediated by dopamine (Crawley J. N. et al., ISIS Atlas of Sci., Pharmac., 1988, 84–90). It is also involved in mechanisms involving acetylcholine, gaba (4-aminobutyric acid), serotonin, opioids, somatostatin or substance P and in ionic channels.

Its administration causes physiological modifications: palpebral prosis, hypothermia, hyperglycaemia or catalepsy, and behavioural modifications: hypolocomotoricity, decrease in exploratory behaviour, analgesia, modification of the ability to learn, modification of sexual behaviour and satiation.

CCK exerts its biological activity via at least two types of receptors: CCK-A receptors, located mainly on the periphery, and CCK-B receptors, present essentially in the cerebral cortex. Peripheral-type CCK-A receptors are also present in certain regions of the central nervous system, including the area postrema, the nucleus of the solitary tract and the interpeduncular nucleus (Moran T. H. et al., Brain Research, 1986, 362, 175–179; Hill D. R. et al., J. Neurosci., 1990, 10, 1070–1081); with, however, differences in type (Hill D. R. et al., J. Neurosci., 1990, 10, 1070–1081; Mailleux P. et al., Neurosci. Lett., 1990, 117, 243–247; Barrett R. W. et al., Mol. Pharmacol., 1989, 36, 285–290; Mercer J. G. et al., Neurosci. Lett., 1992, 137, 229–231; Moran T. H. et al., TIPS, 1991, 12, 232–236).

At the periphery, via CCK-A receptors (Moran T. H. et al., Brain Research, 1986, 362, 175–179), CCK delays gastric dumping, modulates intestinal motility, stimulates vesicular contraction, increases bile secretion and controls pancreatic secretion (McHugh P. R. et al., Fed. Proc., 1986, 45, 1384–1390; Pendleton R. G. et al., J. Pharmacol. Exp. Ther., 1987, 241, 110–116).

CCK could have an effect, in certain cases, on arterial pressure and could influence the immune systems.

The role of CCK in the signal for satiation is supported by the fact that the CCK plasma concentrations, which depend on the composition of the meals (high concentrations of proteins or lipids), are, after the meals, greater than those observed before the meals (Izzo R. S. et al., Regul. Pept., 1984, 9, 21–34; Pfeiffer A. et al., Eur. J. Clin. Invest., 1993, 23, 57–62; Lieverse R. J.). Significantly high CCK plasma levels have been described in anorexic and/or bulimic patients (Philipp E. et al., Life Sc., 1991, 48, 2442–2450; Geraciotti T. D. Jr. et al., N. Engl. J. Med., 1988, 319, 683–688). In bulimic patients, there is a decrease in the secretion of CCK induced by a meal and a lowering in CCK concentrations in the cerebrospinal fluid (Geraciotti T. D. Jr. et al., N. Engl. J. Med., 1988, 319, 683–688).

On the basis of this evidence of the key role of CCK in the peripheral signal for satiation, the usefulness of agonists and antagonists of CCK as medicine in the treatment of certain disorders of food behaviour, of obesity and of diabetes is indisputable. An agonist of CCK receptors can also be used in therapeutics in the treatment of disorders of emotional, sexual and memory behaviour (Itoh S. et al., Drug. Develop. Res., 1990, 21, 257–276), of schizophrenia, of psychoses (Crawley J. N. et al., ISIS Atlas of Sci., Pharmac., 1988, 84–90 and Crawley J. N., TIPS, 1991, 12, 232–265), of Parkinson's disease, of tardive dyskinesias and of various disorders of the gastrointestinal sphere (Drugs of the Future, 1992, 17(3), 197–206).

Agonists of the CCK receptor are described in the literature. For example, certain products having such properties are described in EP-A-0,383,690 and WO 90/06937.

The majority of the CCK-A agonists described to date have a peptide nature. Thus, FPL 14294, derived from CCK-7, a powerful CCK-A agonist which is nonselective with respect to CCK-B receptors, has a powerful inhibiting activity on food uptake in rats and in dogs, after intranasal administration (Simons R. D. et al., Pharmacol. Biochem. Behav., 1994, 47(3), 701–708; Kaiser E. F. et al., FASEB, 1991, 5, A864). Likewise, it has been shown that A-71623, a tetrapeptide which is a selective agonist of CCK-A receptors, is effective in anorexia models over a period of 11 days and results in a significant reduction in weight gain with respect to the control in rodents and cynomolgus monkeys (Asin K. E. et al., Pharmacol. Biochem. Behav., 1992, 42, 699–704). In the same way, structural analogues of A 71623, which are highly effective and selective for CCK-A receptors, possess a powerful anorexigenic activity in rats (Elliott R. L. et al., J. Med. Chem., 1994, 37, 309–313; Elliott R. L. et al., J. Med. Chem., 1994, 37, 1562–1568).

Patent Application WO 91/13874 describes a series of glycinamide derivatives having an affinity for CCK receptors. More particularly, these compounds are described as selective antagonists of the CCK-B/gastrin receptor (XIIth Int. Symp. Med. Chem., Basle, 1992).

It has now surprisingly been found that a series of glycinamide derivatives has a powerful agonist activity for CCK-A receptors.

The compounds according to the invention have formed the subject of systematic studies in order to characterize:

their potentiality in displacing [$^{125}$I]-CCK from its binding sites present on rat pancreas membranes (CCK-A receptor) or from 3T3 cells expressing the recombinant human CCK-A receptor, their selectivity with respect to the CCK-B receptor present on guinea pig cortex membranes, the compounds being selective or non-selective ligands of CCK-A receptors, their agonist property towards CCK-A receptors, through their ability to induce the in vitro secretion of amylase by rat pancreas cells or to cause the in vivo dumping of the gall bladder in mice or, still in vivo, to block gastric dumping in mice, their effect on food consumption in rats.

Thus, the present invention relates to compounds of formula:

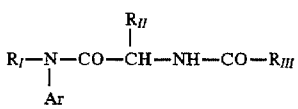

in which
- $R_I$ represents a ($C_3$–$C_8$) alkyl; an arylalkyl -Alk-$Ar_1$, where Alk represents an alkylene containing 1 to 4 carbon atoms and $Ar_1$ represents a phenyl group or a heterocycle optionally substituted by a halogen, a ($C_1$–$C_3$) alkyl, a ($C_1$–$C_3$) alkoxy, a trifluoromethyl or a hydroxyl; a cycloalkylalkyl in which the alkyl is ($C_1$–$C_4$) and the cycloalkyl is ($C_3$–$C_{10}$); a ($C_3$–$C_{10}$) cycloalkyl optionally substituted by a hydroxyl, a ($C_1$–$C_3$) alkoxy or a ($C_1$–$C_3$) alkyl, it being possible for the said alkyl to substitute the same carbon atom twice; an alkoxyalkyl in which the alkoxy is ($C_1$–$C_4$) and the alkyl is ($C_2$–$C_5$); or a group (AB)N—CO—($CH_2$)$_r$—, where A is a ($C_1$–$C_3$) alkyl, B is a ($C_1$–$C_3$) alkyl or a phenyl or else A and B form, with the nitrogen atom to which they are bonded, a heterocycle chosen from pyrrolidine, piperidine and morpholine, and R is 1, 2 or 3;
- $R_{II}$ represents hydrogen; a ($C_1$–$C_6$) alkyl; a ($C_1$–$C_5$) hydroxyalkyl; a group —($CH_2$)$_m$—$COR_2$ in which m is an integer from 1 to 3 and $R_2$ represents a hydroxyl, a ($C_1$–$C_4$) alkoxy group, a benzyloxy group or a group —$NR_3R_4$ in which $R_3$ or $R_4$ independently represent hydrogen, a ($C_1$–$C_4$) alkyl or constitute, with the nitrogen atom to which they are bonded, a heterocycle chosen from pyrrolidine, piperidine and morpholine; an aralkyl group —($CH_2$)$_n$—$Ar_2$ in which n is equal to 0 or represents an integer from 1 to 4 and $Ar_2$ represents a phenyl or a heterocycle optionally substituted by a halogen, a ($C_1$–$C_3$) alkyl, a ($C_1$–$C_3$) alkoxy, a trifluoromethyl, a hydroxyl or a benzyloxy; a cycloalkylalkyl in which the alkyl is ($C_1$–$C_4$) and the cycloalkyl is ($C_3$–$C_{10}$); a ($C_1$–$C_4$) aminoalkyl; a group R—CO—NH—($CH_2$)$_x$— in which x represents an integer from 1 to 4 and R represents a ($C_1$–$C_4$) alkyl, a phenyl, a benzyl, a 2-phenylethenyl or a benzyloxy, the aromatic rings optionally being substituted by a halogen, a ($C_1$–$C_3$) alkyl, a ($C_1$–$C_3$) alkoxy, a trifluoromethyl, a hydroxyl or a sulpho or carboxyl group; a guanidino($C_1$–$C_4$)alkyl; an imidazolyl ($C_1$–$C_3$) alkyl; an alkylthioakyl in which the alkyls are ($C_1$–$C_3$); an aralkylthioalkyl in which the aryl part is optionally heterocyclic and the alkyl parts are ($C_1$–$C_3$), the aryl optionally being substituted by a halogen, a ($C_1$–$C_3$) alkyl, a ($C_1$–$C_3$) alkoxy, a trifluoromethyl or a hydroxyl; a benzyloxyalkyl in which the alkyl is ($C_1$–$C_3$) and the phenyl is optionally substituted by a halogen, a hydroxyl, a ($C_1$–$C_3$) alkoxy, a ($C_1$–$C_3$) alkyl, a trifluoromethyl, a nitrile or a nitro;
- $R_{III}$ represents a naphthyl group; a quinolyl group; an isoquinolyl group; an indolyl group which is unsubstituted, substituted on a carbon or substituted on the nitrogen by a ($C_1$–$C_4$) alkylcarbonyl group, by a group —($CH_2$)$_p$—$COR_5$, p being an integer from 0 to 4 and $R_5$ representing $OR'_5$ or $NR'_5R''_5$ with $R'_5$ and $R''_5$, which may or may not be identical, representing hydrogen or a ($C_1$–$C_4$) alkyl or else $R'_5$ and $R''_5$ form, together with the nitrogen atom to which they are bonded, a piperidine, by a ($C_1$–$C_4$) hydroxyalkyl, by a ($C_2$–$C_6$) alkoxyalkyl, by a ($C_2$–$C_4$) cyanoalkyl, by a tetrahydropyranyl, by an adamantylaminocarbonyl ($C_1$–$C_4$) alkyl or by a chain —($CH_2$)$_q$—, q being an integer from 2 to 4, one of the carbons of which substitutes the phenyl ring of the indole group in order to constitute a ring;

Ar represents a 2-methoxy-3-pyridyl, 4-methoxy-5-pyrimidinyl or 2-methoxyphenyl group containing at least two other substituents chosen from a ($C_1$–$C_3$) alkyl, a ($C_1$–$C_3$) alkoxy, a halogen atom and a trifluoromethyl; or Ar represents a naphthyl group;

or else $R_I$ and $R_{II}$ together constitute a group

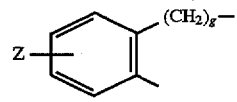

in which g represents 0, 1 or 2 and Z represents a ($C_1$–$C_4$) alkyl, a ($C_1$–$C_3$) alkoxy or a halogen;

or optionally one of their salts.

One advantageous class of products is represented by the following formula:

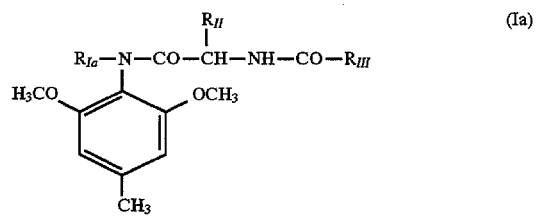

in which $R_{II}$ and $R_{III}$ are as defined above for (I) and $R_{Ia}$ represents a ($C_5$–$C_8$) alkyl; an arylalkyl -Alk-$Ar_1$, where Alk represents an alkylene containing 1 to 4 carbon atoms and $Ar_1$ represents a phenyl group or a heterocycle optionally substituted by a halogen, a ($C_1$–$C_3$) alkyl, a ($C_1$–$C_3$) alkoxy, a trifluoromethyl or a hydroxyl; a cycloalkylalkyl in which the alkyl is ($C_1$–$C_4$) and the cycloalkyl is ($C_3$–$C_{10}$); a ($C_3$–$C_{10}$) cycloalkyl which is optionally substituted by a ($C_1$–$C_3$) alkoxy, a hydroxyl or a ($C_1$–$C_3$) alkyl, it being possible for the said alkyl to substitute the same carbon atom twice; an alkoxyalkyl in which the alkoxy is ($C_1$–$C_4$) and the alkyl is ($C_2$–$C_5$); or a group (AB)N—CO—($CH_2$)$_r$—, where A is a ($C_1$–$C_3$) alkyl, B is a ($C_1$–$C_3$) alkyl or a phenyl or else A and B form, with the nitrogen atom to which they are bonded, a heterocycle chosen from pyrrolidine, piperidine and morpholine, and r is 1, 2 or 3, or optionally one of their salts.

The addition salts of these compounds are those obtained, if appropriate, with inorganic or organic acids and bases; the nontoxic pharmaceutically acceptable salts are preferred but other salts, which can be used for isolating or purifying the compounds of formula (I) are also within the invention.

In the preceding and following definitions, the alkyl radicals are straight- or branched-chain.

When $Ar_1$ or $Ar_2$ represents a heterocycle, this heterocycle is preferably selected from pyridine, pyrimidine, pyrazine or pyridazine.

When $R_{II}$ represents aralkylthioalkyl, the aryl group is preferably selected from phenyl, pyridine, pyrimidine, pyrazine and pyridazine.

In the formula (I), the halogen atoms are preferably chlorine, bromine or fluorine atoms.

The compounds of formula (I) containing one or a number of asymmetric centres exhibit isomeric forms. The racemics and the enantiomers or stereoisomers of these compounds also form part of the invention.

When the substituent $R_{II}$ is other than hydrogen, the enantiomers in which the carbon carrying $R_{II}$ is in the R configuration are preferred.

When $R_I$ and $R_{II}$ together constitute a group

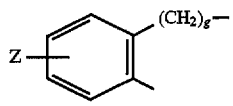

in which Z and g are as defined for (I), the enantiomers in which the carbon carrying $R_{II}$ is in the S configuration are preferred.

A group of compounds having a better agonist activity for CCK-A receptors is that in which $R_I$ represents a ($C_3$–$C_8$) alkyl, better still is that in which $R_I$ represents a ($C_4$–$C_8$) alkyl and a preferred group is that in which $R_I$ represents a ($C_5$–$C_8$) alkyl and a particularly preferred group is that in which $R_I$ is a ($C_5$–$C_7$) cycloalkyl.

The compounds of formula (I) in which Ar represents a naphthyl group and $R_I$ is $R_{Ia}$ as defined above form another group of preferred compounds.

The compounds of formula (I) in which Ar represents a 2-methoxyphenyl radical substituted by at least two substituents, chosen from ($C_1$–$C_4$) alkyl, ($C_1$–$C_3$) alkoxy, a halogen atom or a trifluoromethyl group, are advantageous compounds.

The compounds of formula (I) in which Ar represents a 2-methoxylohenyl radical substituted on the aromatic ring by a methyl and a second methoxy are very advantageous compounds.

The compounds of formula (I) in which $R_{III}$ represents a 2-indolyl which may or may not be substituted on the N are particularly advantageous.

The compounds of formula (I) in which $R_I$ represents a $C_5$ alkyl or a $C_6$ cycloalkyl, $R_{II}$ represents a benzyloxyalkyl or a cycloalkylalkyl, $R_{III}$ represents a substituted 2-indolyl and Ar represents a 2,6-dimethoxy-4-methylphenyl are more particularly preferred.

The following compounds are even more particularly preferred:

EXAMPLE 3

(R)-N-[1-[(2,6-Dimethoxy-4-methylphenyl)pentylcarbamoyl]ethyl]-1H-indole-2-carboxamide

EXAMPLE 6

3-[2-[[(Cyclohexylmethyl)(2,6-dimethoxy-4-methylphenyl)carbamoyl]methylcarbamoyl]indol-1-yl]propionic acid

EXAMPLE 8

N-{[(2,6-Dimethoxy-4-methylphenyl)pentylcarbamoyl]methylcarbamoyl}-1H-indole-2-carboxamide

EXAMPLE 9

Methyl{2-[[(2,6-dimethoxy-4-methylphenyl)pentylcarbamoyl]methylcarbamoyl]indol-1-yl}acetate

EXAMPLE 10

{2-[[(2,6-Dimethoxy-4-methylphenyl)pentylcarbamoyl]methylcarbamoyl]indol-1-yl}acetic acid

EXAMPLE 13

(R)-[2-{1-[(2,6-Dimethoxy-4-methylphenyl)pentylcarbamoyl]ethylcarbamoyl}indol-1-yl]acetic acid

EXAMPLE 16

(R)-4-{(2,6-Dimethoxy-4-methylphenyl)pentylcarbamoyl}-4-[(1H-indole-2-carbonyl)amino]butyric acid

EXAMPLE 19

(R)-N-{1-[(2,6-Dimethoxy-4-methylphenyl)pentylcarbamoyl]-2-(4-hydroxyphenyl)ethyl}-1H-indole-2-carboxamide

EXAMPLE 28

(R)-4-[(1-Carboxymethyl-1H-indole-2-carbonyl)amino]-4-[(2,6-dimethoxy-4-methylphenyl)pentylcarbamoyl]butyric acid

EXAMPLE 30

(R)-{2-[{1-{(2,6-Dimethoxy-4-methylphenyl)pentylcarbamoyl}-2-phenylethyl}carbamoyl]indol-1-yl}acetic acid

EXAMPLE 31

(R)-[2-{[1-{(2,6-Dimethoxy-4-methylphenyl)pentylcarbamoyl}-2-(4-hydroxyphenyl)ethyl]carbamoyl}indol-1-yl]acetic acid

EXAMPLE 32

(R)-[2-{[2-(Carbamoyl)-1-{(2,6-dimethoxy-4-methylphenyl)pentylcarbamoyl}ethyl]carbamoyl}indol-1-yl]acetic acid

EXAMPLE 33

(R)-[2-{[3-(Carbamoyl)-1-{(2,6-dimethoxy-4-methylphenyl)pentylcarbamoyl}propyl]carbamoyl}indol-1-yl]acetic acid

EXAMPLE 44

Sodium (R)-[2-{[1-{(2,6-dimethoxy-4-methylphenyl)pentylcarbamoyl}-2-(benzyloxy)ethyl]carbamoyl}indol-1-yl]acetate

EXAMPLE 51

Sodium (R)-{2-[{1-[(2,6-dimethoxy-4-methylphenyl)pentylcarbamoyl]-2-(cyclohexyl)ethyl}carbamoyl]indol-1-yl}acetate

EXAMPLE 81

(R)-{2-[{1-[(2,6-Dimethoxy-4-methylphenyl)
pentylcarbamoyl]-2-(benzylthio)ethyl}carbamoyl]
indol-1-yl}acetic acid

EXAMPLE 82

(R)-{2-[{1-[(2,6-Dimethoxy-4-methylphenyl)
pentylcarbamoyl]-3-(phenyl)propyl}carbamoyl]
indol-1-yl}acetic acid

EXAMPLE 85

[2-{[(6-Chloro-2,4-dimethoxy-5-methylphenyl)
pentylcarbamoyl]methylcarbamoyl}indol-1-yl]acetic
acid

EXAMPLE 94

Sodium[2-{[(5-chloro-2-methoxy-4-methylphenyl)
pentylcarbamoyl]methylcarbamoyl}indol-1-yl]
acetate

EXAMPLE 103

[2-{[(2,5-Dimethoxy-4-methylphenyl)
pentylcarbamoyl]methylcarbamoyl}indol-1-yl]acetic
acid

EXAMPLE 109

N-{[(Isopentyl)(2,4,6-trimethoxyphenyl)carbamoyl]
methyl}-1H-indol-2-carboxamide

EXAMPLE 112

Sodium[2-{[(benzyl)(2,6-dimethoxy-4-
methylphenyl)carbamoyl]methylcarbamoyl}indol-1-
yl]acetate

EXAMPLE 118

[2-{[(Cyclohexylmethyl)(2,6-dimethoxy-4-
methylphenyl)carbamoyl]methylcarbamoyl}indol-1-
yl]acetic acid

EXAMPLE 126

N-{[(2,6-Dimethoxy-4-methylphenyl)
pentylcarbamoyl]methyl}-2-
naphthalenecarboxamide

EXAMPLE 127

N-{[(2,6-Dimethoxy-4-methylphenyl)
pentylcarbamoyl]methyl}-3-quinolinecarboxamide

EXAMPLE 137

8-{[(2,6-Dimethoxy-4-methylphenyl)(3-
methoxypropyl)carbamoyl]methylcarbamoyl}-5,6-
dihydro-4H-pyrrolo[3,2,1-ij]quinoline

EXAMPLE 138

Methyl{2-[[(1-naphthyl)pentylcarbamoyl]
methylcarbamoyl]indol-1-yl}acetate

EXAMPLE 139

{2-[[(1-Naphthyl)pentylcarbamoyl]
methylcarbamoyl]indol-1-yl}acetic acid

EXAMPLE 141

(R)-[2-{1-[{N-(2,6-Dimethoxy-4-methylphenyl)-N-
cyclohexyl}carbamoyl]ethylcarbamoyl}indol-1-yl]
acetic acid

EXAMPLE 155

(R)-[2-{[1-{[N-(2,6-Dimethoxy-4-methylphenyl)-N-
cyclohexyl]carbamoyl}-2-(benzyloxy)ethyl]
carbamoyl}indol-1-yl]acetic acid

EXAMPLE 168

(R)-[2-{[1-{[N-(2,6-Dimethoxy-4-methylphenyl)-N-
cyclohexyl]carbamoyl}-2-(cyclohexyl)ethyl]
carbamoyl}indol-1-yl]acetic acid

EXAMPLE 171

(R)-[2-{[1-{[N-(2,6-Dimethoxy-4-methylphenyl)-N-
cyclohexylmethyl]carbamoyl}-2-(cyclohexyl)ethyl]
carbamoyl}indol-1-yl]acetic acid

EXAMPLE 172

(R)-{2-[{1-[(2,6-Dimethoxy-4-methylphenyl)
butylcarbamoyl]-2-(benzyloxy)ethyl}carbamoyl]
indol-1-yl}acetic acid

EXAMPLE 192

(R)-{2-[N-{1-[(2,6-dimethoxy-4-methylphenyl)
pentylcarbamoyl]-5-(cinnamoylamino)
pentyl}carbamoyl]indol-1-yl}acetic acid The compounds according to the invention are prepared
according to the following reaction scheme:

Scheme 1

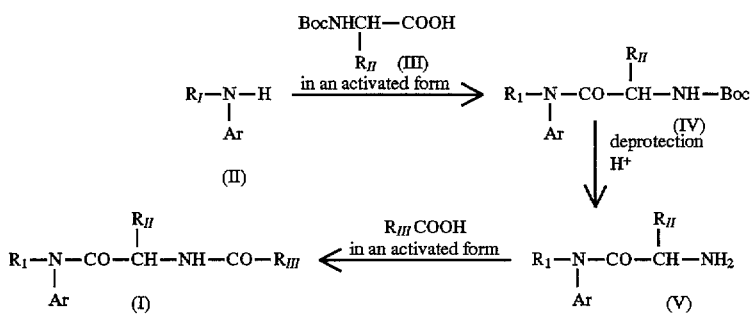

According to another of its aspects, the present invention relates to a process for the preparation of the compounds of formula (I) characterized in that an amine of formula:

in which Ar and $R_I$ are as defined above, is treated with an N-protected amino acid of formula:

in which $R_{II}$ is as defined for (I) and in which, if appropriate, the reactive groups of $R_{II}$ have been protected, in order to lead to a compound of formula:

in which $R_I$, Ar and $R_{II}$ are as defined above, in order to lead to a compound (I) according to the invention or one of its salts.

The starting compounds of formulae (II) are either commercially available or prepared according to known methods, for example:

for 2,6-dimethoxy-4-methylaniline, according to an adaptation of the process described by Mori S. et al. Tet. Lett., 1984, 25, 429;

for 2,4-dimethoxy-5-methylaniline, according to Sargent M. V., J. Chem. Soc. Perkins Trans I, 1982, 1095;

for 2,4,6-trimethoxyaniline, according to EP-A-088849;

for 2,5-dimethoxy-4-methylaniline, according to Shaikh Y. A., J. Heterocyclic Chem., 1977, 14, 1049;

for 2,6-dimethoxy-4-trifluoromethylaniline, according to an adaptation of the process described by Mori S. et al., Tet. Lett., 1984, 25, 429 from 1,5-dimethoxy-3-trifluoromethylbenzene prepared according to Robertson A. et al., J. Chem. Soc., 1951, 2013;

for 4-chloro-2,6-dimethoxyaniline, according to Hodgson H. et al., J. Chem. Soc., 1934, 1433;

for 1-amino-2,6-dimethoxy-4-methylpyrimidine, according to Urban R. et al., Holv. Chim. Acta, 1958, 41, 1806;

for the compound of formula:

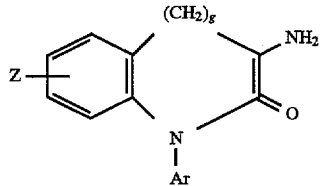

according to EP-0,572,235.

When $R_I$ is other than a cycloalkyl, the anilines of formula (II) or the compounds of formula (IV) in which Ar is as defined for (I) can be prepared according to known methods according to the following Scheme 2:

Scheme 2

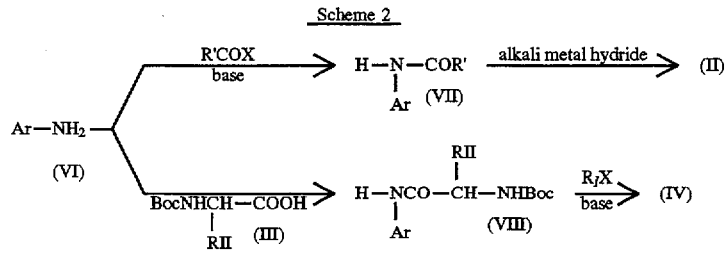

either by acylation of a compound of formula:

in which Ar is as defined for (I), with an acid halide of formula R'—CO—X, in which X represents a chlorine or bromine atom and R' is such that R'—$CH_2$— represents $R_I$ as defined for (I), or with one of its activated esters, in the presence of an organic base such as triethylamine or N-ethylmorpholine, in organic solvents such as diethyl ether, dichloromethane, chloroform, dimethylformamide or tetrahydrofuran, in order to lead to a compound of formula:

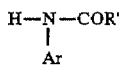    (VII)

in which R' and Ar as defined above, in order subsequently to reduce it with an alkali metal hydride such as lithium aluminium hydride, in an inert organic solvent such as diethyl or diisopropyl ether or tetrahydrofuran, in order to lead to a compound of formula (II), or by coupling of the compound (VI) with an N-protected amino acid, which has been activated beforehand, of formula (III), in order to lead to a compound of formula:

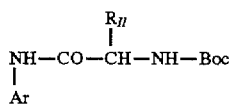    (VIII)

in which $R_{II}$ and Ar are as defined for (I), which is then N-alkylated, after generation of the anion with a strong base, in order to obtain a compound of formula:

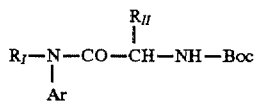    (IV)

in which $R_I$, $R_{II}$ and Ar are as defined for (I), this compound then being treated in anhydrous acidic medium in order to provide a compound (V) in the salt form of formula:

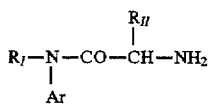    (V)

which is then acylated with an acid of formula $R_{III}COOH$, which has been activated beforehand, in order to lead to a compound (I) according to the invention or one of its optional salts.

When $R_I$ represents a cycloalkyl, the anilines of formula (II) are novel and can be prepared independently according to one of Schemes 3, 4 or 5 below.

Scheme 3

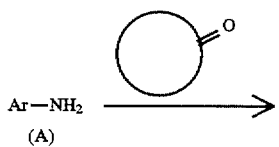

-continued
Scheme 3

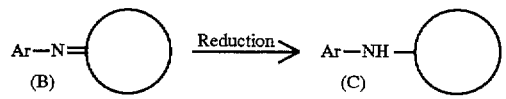

The coupling reaction of the aniline (A), in which Ar is as defined for (I), with the cycloalkanone leads to the Schiff base (B) which is then reduced according to the usual conditions, for example by reacting with a sodium borohydride in ethanol or by reacting with formic acid at reflux.

Scheme 4

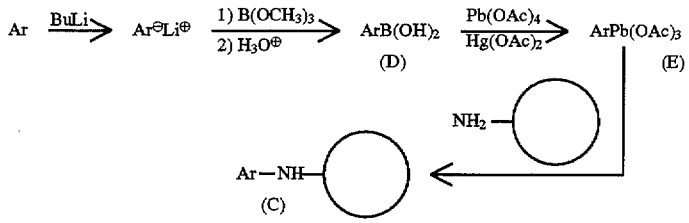

This synthesis is an adaptation of the process described by J. T. Pinkey et al., J. Chem. Soc. Perkin Trans I, 1990, 715 for the preparation of the compounds (D) and (E) and of the process described by D. H. R. Barton et al., Tet. Lett., 1987, 28(27), 3111.

Scheme 5

The amino acids used are activated by the coupling reagents commonly used in peptide chemistry, for example, in the case of racemic amino acids or amino acids which do not have an asymmetric centre: $BOP/NEt_3$, $BOP-Cl/NEt_3$, $DCC/HOBT/NEt_3$ or mixed anhydride with ClCOOiBu in the presence of triethylamine and, in the case of R or S enantiomers of amino acids, in the presence of BOP/N-ethylmorpholine or $Boc_2O$/pyridine.

The anions of the compounds (VIII) are generated by strong bases such as, for example, sodium hydride or potassium tert-butoxide in an aprotic anhydrous solvent, such as tetrahydrofuran.

The compounds (V) are obtained from the acetanilides (IV) in anhydrous acidic medium such as trifluoroacetic acid in dichloromethane or gaseous hydrochloric acid in solution in ethyl acetate, for example.

The compounds (V) are then isolated in the hydrochloride or trifluoroacetate form, for example.

The compounds (I) are obtained by the conventional methods for peptide coupling between the compounds (V) and the acids $R_{III}COOH$, which have been activated beforehand in the form of an acid halide, in the form of a mixed anhydride, with, for example, ClCOOiBu, or in the form of an activated ester with $BOP/NEt_3$, BOP/N-ethylmorpholine, $BOP-Cl/NEt_3$, $DCC/HOBT/NEt_3$, $Boc_2O$/pyridine, according to methods which are well known to a person skilled in the art.

The optional salts of the compounds of formula (I) with organic or inorganic acids or bases are prepared in the usual way by introducing the acid, or the base, into a solution of the compound of formula (I).

The salt is isolated, depending on its solubility characteristics, after evaporation of the solvent or addition of a nonsolvent.

The compounds of formula (V) in which $R_I$, Ar and $R_{II}$ are as defined above for (I) are novel and constitute one of the subjects of the invention.

Another subject of the invention, according to another of its aspects, is pharmaceutical compositions comprising the above compounds (I).

More generally, the compounds of formula (I) have formed the subject of in vitro binding studies relating to CCK receptors.

A study of the agonist effect of the compounds on the secretion of amylase was carried out as follows. Pancreas acini are obtained by enzymatic digestion (collagenase) of the pancreas of a rat which has fasted for 18 hours. Aliquots (485 µl) are incubated at 37° C. for 30 minutes in the presence of increasing concentrations of agonist according to Jensen et al., J. Biol. Chem., 1982, 257 (10), 5554. Incubation is halted by centrifuging for 15 seconds. The supernatant is stored in an ice bath in order to measure the amylase level according to the technique of Ceska et al., Clin. Chim. Acta., 1969, 26, 437 (reagent Phadebas®: amylase test marketed by Pharmacia Diagnostic). The compounds to be tested are dissolved in dimethyl sulphoxide and then in an incubation buffer.

The compounds of formula (I) behave as agonists of CCK-A receptors with $EC_{50}$ values (effective concentration inducing 50% of the amylase secretion compared with a maximum effect produced in the presence of CCK) of about $10^{-7}$ to $10^{-9}$M.

A study of the agonist effect of the compounds on the contraction of the gall bladder was carried out as follows. Female albino Swiss CD1 mice (20–25 g) are fasted from solid food for 24 hours. On the day of the experiment, the products (in suspension in a 1% carboxymethyl cellulose or 0.6% methyl cellulose solution) or the corresponding vehicle are administered orally. The mice are sacrificed by cervical dislocation one hour after administration of the products and the gall bladders are removed and weighed. The results are expressed in mg/kg of bodyweight (Europ. J. Pharmacol., 1993, 232, 13–19).

The compounds of formula (I) completely contract the gall bladder, like CCK itself, and therefore behave as agonists of CCK-A receptors. Some of them have $ED_{50}$ values (effective dose inducing 50% of the decrease in weight of the bladders observed with CCK) of less than 3 mg/kg orally.

A study of the agonist effect of the compounds on gastric dumping was carried out as follows. Female albino Swiss CD1 mice (20–25 g) are fasted from solid food for 18 hours. On the day of the experiment, the products (in suspension in a 1% carboxymethyl cellulose or 0.6% methyl cellulose solution) or the corresponding vehicle are administered intraperitoneally 30 minutes before administration of a charcoal meal (0.3 ml per mouse of a suspension, in water, of 10% of charcoal powder, 5% of gum arabic and 1% of carboxymethyl cellulose). The mice are sacrificed 5 minutes later by cervical dislocation and gastric dumping is defined as the presence of charcoal in the intestine beyond the pyloric sphincter (Europ. J. Pharmacol., 1993, 232, 13–19).

The compounds of formula (I) completely block gastric dumping, like CCK itself, and therefore behave as agonists of CCK receptors. Some of them have $ED_{50}$ values (effective dose inducing 50% of the effect of CCK) of less than 1 mg/kg intraperitoneally.

A study of the CCK agonist effect of the compounds on food consumption was carried out as follows. Male Sprague Dawley (Charles River, France) rats (200–240 g) are isolated 10 days before the experiment and are subjected, each day, successively to 18 hours of fasting and 6 hours of feeding: food is available from 1000 hours to 1600 hours and water is available ad libitum. On the day of the experiment, the products (in suspension in a 0.6% methyl cellulose solution) or the vehicle are administered intraperitoneally.

Thirty minutes after the treatment (at 10 hours), a known amount of food is introduced into the cage: food consumption is measured 1 hour and 3 hours later.

The compounds of formula (I) decrease food uptake and therefore behave as agonists of CCK-A receptors (Gibbs J. et al., J. Comp. Physiol. Psychol., 1973, 488–495).

Some of them are active at the oral dose of 3 mg/kg, at which dose they reduce food consumption by 30 to 40% with respect to a control animal.

Consequently, the compounds of formula (I) are used as agonists of CCK-A receptors for the preparation of medicines intended for combating diseases whose treatment requires stimulation by total or partial agonism of cholecystokinin receptors, more particularly for the manufacture of medicines intended for the treatment of certain disorders of food behaviour, of obesity, of diabetes, of disorders of emotional, sexual and memory behaviour, of psychoses and in particular schizophrenia, of Parkinson's disease, of tardive dyskinesia and of various disorders of the gastrointestinal sphere.

The compounds of formula (I) have little toxicity; their toxicity is compatible with their use as medicines for the treatment of the above disorders and diseases.

The compounds of formula (I) can be formulated in pharmaceutical compositions for administration to mammals, including man, for the treatment of the abovesaid diseases.

The compounds of formula (I) above and their pharmaceutically acceptable salts can be used at daily doses of 0.01 to 100 mg per kilo of body weight of the mammal to be treated, preferably at daily doses of 0.1 to 50 mg/kg.

In man, the dose can preferably vary from 0.5 to 4,000 mg per day, more particularly from 2.5 to 1,000 mg, according to the age of the subject to be treated or the type of treatment: prophylactic or curative.

In the pharmaceutical compositions of the present invention, the active principle is generally formulated in dosage units containing from 0.5 to 1,000 mg, advantageously from 1 to 500 mg and preferably from 2 to 200 mg of the said active principle per dosage unit.

Another subject of the present invention is therefore pharmaceutical compositions which contain, as active principle, one of the above compounds. These compositions are prepared so as to be able to be administered by the digestive or parental route.

In the pharmaceutical compositions of the present invention for oral, sublingual, subcutaneous, intramuscular, intravenous, transdermal, local or rectal administration, the active ingredient can be administered in unit administration forms, as a mixture with conventional pharmaceutical vehicles, to animals and to man. The appropriate unit administration forms comprise oral forms, such as tablets, gelatin capsules, powders, granules and oral solutions or suspensions, sublingual and buccal administration forms, subcutaneous, intramuscular, intravenous, intranasal or intraocular administration forms and rectal administration forms.

When a solid composition is prepared in the form of tablets, the main active ingredient is mixed with a pharmaceutical vehicle, such as gelatin, starch, lactose, magnesium stearate, talc, gum arabic or similar. The tablets can be coated with sucrose or other appropriate materials or alternatively they can be treated so that they have a prolonged or delayed activity and so that they continuously release a predetermined amount of active principle.

A gelatin capsule preparation is obtained by mixing the active ingredient with a diluent and by pouring the mixture obtained into soft or hard gelatin capsules.

A preparation in the syrup or elixir form can contain the active ingredient jointly with a sweetener, preferably a calorie-free one, methylparaben and propylparaben as antiseptic, as well as an agent giving taste and an appropriate dye.

Water-dispersible granules or powders can contain the active ingredient as a mixture with dispersing agents or wetting agents or suspending agents, such as polyvinylpyrrolidone, as well as with sweeteners or taste correctors.

For rectal administration, recourse is made of suppositories which are prepared with binders which melt at rectal temperature, for example cocoa butter or polyethylene glycols.

For parental, intranasal or intraocular administration, use is made of aqueous suspensions, isotonic saline solutions or sterile and injectable solutions which contain pharmacologically compatible dispersing agents and/or wetting agents, for example propylene glycol or butylene glycol.

The active principle can also be formulated in the form of microcapsules, optionally with one or a number of vehicles or additives.

The active principle can also be presented in the form of a complex with a cyclodextrin, for example α-, β- or γ-cyclodextrin, 2-hydroxypropyl-β-cyclodextrin or methyl-β-cyclodextrin.

In what follows, a description is given of EXAMPLES of the implementation of the invention, as well as of the preparations of some synthetic intermediates of formula (II), (IV), (V), (VII) and (VIII). The melting points indicated were determined in capillary tubes.

PREPARATION I
Compound 1—Intermediate of formula (II)

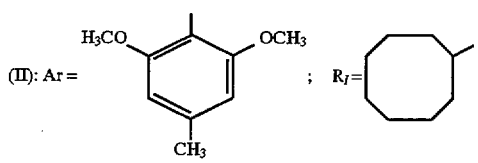

Stage 1

4.2 g of 2,6-dimethoxy-4-methylaniline are dissolved in 50 ml of toluene, 2.45 g of cyclohexanone are then added and the reaction mixture is heated at reflux for 18 hours. The water which is formed is removed as it is formed in the reaction mixture using a Dean and Stark apparatus. The toluene is evaporated and the oily N-cyclohexylidene-2,6-dimethoxy-4-methylaniline residue obtained is used without addition of purification in the following stage.

Stage 2 a) Reduction of the alkylidene with formic acid:

The alkylidene obtained above is dissolved in 50 ml of toluene and 1.15 g of formic acid are added thereto dropwise, under an inert atmosphere. The reaction mixture is heated at reflux under an inert atmosphere for 4 hours. After cooling, the reaction mixture is poured in 100 ml of a 2N aqueous sodium hydroxide solution and then extraction is carried out with ethyl acetate. The organic extracts are dried over anhydrous sodium sulphate and evaporated to dryness. The residual oil is purified by flash chromatography on a colum of silica gel, eluent: dichloromethane/methanol 98/2 (v/v), to provide an oil, Yield: 80%. The oil is converted to the hydrochloride by addition of a 5N solution of hydrogen chloride gas in diethyl ether, white crystals, M.p.=199° C. (hydrochloride).

b) Reduction of the alkylidene with NaBH$_4$

The alkylidene obtained in Stage 1 is dissolved in 50 ml of ethanol and 0.95 g of sodium borohydride is added thereto in small portions, under an inert atmosphere, and the reaction mixture is left at room temperature for 2 hours. 20 ml of acetone are added to the reaction mixture, which is evaporated to dryness. The residue is taken up in water and the aqueous phase is extracted with dichloromethane. The organic extracts are dried over anhydrous sodium sulphate and evaporated to dryness. The oily residue is chromatographed on a column of silica gel, eluent: dichloromethane/methanol 98/2 (v/v). The oil obtained is converted to N-cyclohexyl-2,6-dimethoxy-4-methylaniline hydrochloride, white crystals, M.p.=199° C. (hydrochloride), Yield: 85%.

Compound 2—Intermediate of formula (II)

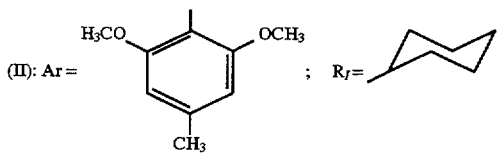

Stage 1

300 ml of a solution (1.6M) of butyllithium in hexane are added dropwise at room temperature to a solution of 73 g of 3,5-dimethoxytoluene in 450 ml of diethyl ether. The reaction mixture is heated at reflux for 3 hours under an inert atmosphere, the reaction mixture is then cooled to −60° C. and 99.7 g of methyl borate are added dropwise over 60 minutes. The reaction mixture is left at −60° C. for 3 hours and left to return to room temperature. The reaction mixture is stirred at room temperature for 16 hours, 6N hydrochloric acid is then added to the reaction mixture (pH=1) and the reaction mixture is left to separate by settling. The organic phase is recovered. The aqueous phase is extracted with diethyl ether. The combined organic phases are dried over anhydrous sodium sulphate. Evaporation of the solvent leaves a yellow oil which crystallizes by cooling to 0° C. After drying, white crystals of 2,6-dimethoxy-4-methylphenylboronic acid are recovered, M.p.=108° C., Yield 80%.

45.4 g of lead tetraacetate and 3.2 g of mercuric acetate are suspended in 150 ml of anhydrous chloroform and the mixture is heated to 40° C. under an argon atmosphere. A solution of 20 g of 2,6-dimethoxy-4-methylphenylboronic acid (prepared above) in 100 ml of chloroform is added dropwise to the reaction mixture at 40° C. The reaction mixture is left for 75 minutes at 40° C. and is then left to return to room temperature while stirring well. The reaction mixture is stirred at room temperature for 18 hours and is then diluted with 800 ml of dichloromethane. The solution is filtered over a bed of celite and the solvent is then evaporated to dryness in order to obtain yellow crystals of 2,6-dimethoxy-4-methylphenyllead triacetate, M.p.=172° C., Yield: 90%.

Stage 2

10.56 g of cyclooctylamine are dissolved in 500 ml of anhydrous dichloromethane and 1.5 g of cupric acetate are added thereto. A solution of 44.2 g of 2,6-dimethoxy-4-methylphenyllead triacetate, prepared above, in 250 ml of anhydrous dichloromethane is added dropwise to the reaction mixture under an inert atmosphere. The reaction mixture is left at room temperature for 18 hours, the heterogeneous mixture is then filtered over a bed of celite and the filtrate is concentrated to 450 ml. The organic phase is washed with water (3 times). The organic phase is extracted with 3×300 ml of 1N hydrochloric acid. The acidic aqeuous phase is basified with a 2N aqueous sodium hydroxide solution (pH=11). The alkaline aqeuous phase is extracted with dichloromethane and the organic extracts are dried over anhydrous sodium sulphate. Evaporation leaves an oil which is purified by flash chromatography on a column of silica gel, eluent:dichloromethane/methanol:99/1 (v/v) in order to obtain N-cyclooctyl-2,6-dimethoxy-4-methylaniline in the form of an oil. Yield: 52%.

Compound 3—Intermediate of formula (II)

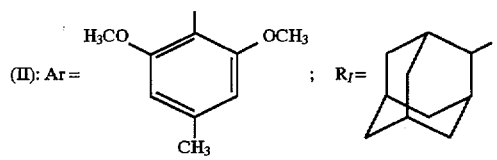

2.1 g of 2,6-dimethoxy-4-methylaniline are dissolved in 10 ml of toluene, 0.5 ml of formic acid is then added to this solution and the mixture is heated to gentle reflux, under inert atmosphere, and 0.93 g of 2-adamantanone, dissolved in 10 ml of toluene, is added dropwise at this temperature. The reaction mixture is heated at reflux for 48 hours, is then evaporated to dryness and the residue is taken up in 30 ml of 2N hydrochloric acid. The insoluble white crystals are filtered and discarded. The acidic filtrate is extracted with dichloromethane. The organic extracts are washed with a 5% aqueous sodium bicarbonate solution and then with water and the organic phases are then dried over anhydrous sodium sulphate. Evaporation leaves a colourless residue which is purified by flash chromatography on a column of silica gel, eluent: toluene/ethyl acetate 7/3 (v/v) in order to obtain N-(2-adamantyl)-2,6-dimethoxy-4-methylaniline; M.p.= 100° C., Yield 52%.

Compound 4—Intermediate of formula (II)

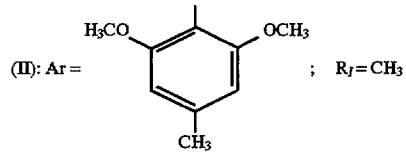

Stage 1

3.4 g of 2,6-dimethoxy-4-methylaniline are dissolved in 40 ml of toluene. 1.03 g of formic acid are added to the solution and the reaction mixture is heated at reflux, under an inert atmosphere, for 24 hours. Evaporation is carried out to dryness and the residue is taken up in 40 ml of 2N hydrochloric acid, stirring is then carried out for 30 minutes at room temperature and the precipitate is filtered and dried. 3.6 g of white crystals of N-formyl-2,6-dimethoxy-4-methylaniline are obtained, M.p.=132° C., Yield: 90%.

Stage 2

6 g of N-formyl-2,6-dimethoxy-4-methylaniline are suspended in 100 ml of tetrahydrofuran and then 33 ml of a 1M solution of lithium aluminium hydride in tetrahydrofuran are added dropwise under an inert atmosphere. The reaction mixture become homogeneous. The reaction mixture is left at room temperature for 2 hours and then, after cooling to 0° C., 1 ml of water, then 1 ml of a 15% aqueous sodium hydroxide solution and then 3 ml of water are successively added dropwise to the reaction mixture. The whole mixture is diluted with 100 ml of ethyl acetate and the precipitate is filtered. The filtrate, evaporated to dryness, leaves an oily residue which is purified by flash chromatography on a column of silica gel, eluent: toluene/ethyl acetate 8/2 (v/v) in order to obtain N-methyl-2,6-dimethoxy-4-methylaniline in the form of an oil, Yield: 85%.

PREPARATION II

Compound 5—Intermediate of formula (VII)

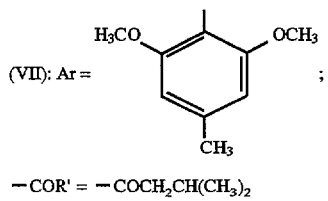

$-COR' = -COCH_2CH(CH_3)_2$ 8.2 g of 2,6-dimethoxy-4-methylaniline are dissolved in 100 ml of diethyl ether at 0° C. under an inert atmosphere, 5.96 g of triethylamine are added to the reaction mixture and then 6.51 g of isovaleryl chloride are added dropwise, while maintaining the temperature at 0° C. The mixture is left at room temperature for 30 minutes and is then poured into 250 ml of water. The aqueous phase is extracted with ethyl acetate after separation by settling of the ethereal phase. The organic phases are combined and washed with water, then dried over anhydrous sodium sulphate and evaporated to dryness. The white crystals of N-(2,6-dimethoxy-4-methylphenyl)isovaleramide obtained are washed with diisopropyl ether; M.p.=139° C., Yield: 92%.

By carrying out the preparations according to PREPARATION II, the intermediate compounds 6 to 25 described below in TABLE A are prepared.

TABLE A

Intermediates of formula (VII)

| Compound | R' | $X_1$ | $X_2$ | $X_3$ | M.p.; °C. |
|---|---|---|---|---|---|
| 6 | $-(CH_2)_3CH_3$ | $OCH_3$ | $OCH_3$ | H | 72 |
| 7 | $-(CH_2)_3CH_3$ | $CH_3$ | $OCH_3$ | H | 101 |
| 8 | $-(CH_2)_3CH_3$ | $OCH_3$ | $CH_3$ | Cl | 138 |
| 9 | $-(CH_2)_3CH_3$ | Cl | $CH_3$ | H | 90 |
| 10 | $-(CH_2)_3CH_3$ | Cl | $OCH_3$ | H | 113 |
| 11 | $-(CH_2)_3CH_3$ | $CH_3$ | Cl | H | 80 |
| 12 | $-(CH_2)_3CH_3$ | $CH_3$ | H | $OCH_3$ | 94 |
| 13 | $-CH_2-CH(CH_3)_2$ | $OCH_3$ | H | $OCH_3$ | 142 |
| 14 | 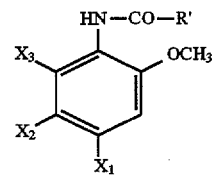 | $CH_3$ | H | $OCH_3$ | 210 |
| 15 | $-(CH_2)_2OCH_3$ | $CH_3$ | H | $OCH_3$ | 116 |

TABLE A-continued

Intermediates of formula (VII)

HN—CO—R' on benzene ring with X3, X2, X1 positions and OCH3

| Compound | R' | X₁ | X₂ | X₃ | M.p.; °C. |
|---|---|---|---|---|---|
| 16 | phenyl | CH₃ | H | OCH₃ | 110 |
| 17 | —CH₂—phenyl | CH₃ | H | OCH₃ | 126 |
| 18 | —(CH₂)₃CH₃ | (VII): Ar = 1-naphthyl | | | 113 |
| 19 | —(CH₂)₃CH₃ | OCH₃ | CH₃ | H | 91 |
| 20 | —(CH₂)₃CH₃ | OCH₃ | H | OCH₃ | 125 |
| 21 | —(CH₂)₂CH₃ | CH₃ | H | OCH₃ | 123 |
| 22 | cyclopropyl | CH₃ | H | OCH₃ | 180 |
| 23 | CH₃ | CH₃ | H | OCH₃ | 156 |
| 24 | cyclopentyl | CH₃ | H | OCH₃ | 178 |
| 25 | H | CH₃ | H | OCH₃ | 132 |

PREPARATION III
Compound 26—Intermediate of formula (II)

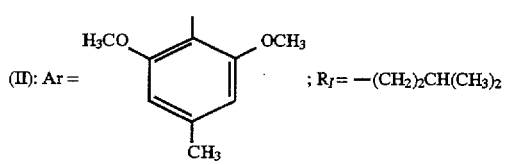

(II): Ar = ; $R_I$ = —(CH₂)₂CH(CH₃)₂

8.5 g of the anilide (compound 5) prepared above are dissolved in 160 ml of dry tetrahydrofuran, which are cooled to 0° C. 34 ml of a 1M solution of lithium aluminium hydride in tetrahydrofuran are added dropwise, the reaction mixture is then left to return to room temperature and is heated at reflux for 2 h 30. It is left to return to room temperature and then cooled to 0° C. 2.5 ml of ice-cold water, 7 ml of a 6N aqueous sodium hydroxide solution and then 2.5 ml of water are successively added to the reaction mixture at 0° C.; the insoluble material is separated by filtration and is washed on a Büchner filter with ethyl acetate. The filtrate is washed with salted water, dried over anhydrous sodium sulphate and evaporated under vacuum. A yellow oil is recovered which is purified by flash chromatography on a column of silica gel, eluent: dichloromethane/diethyl ether 98/2 (v/v) in order to provide N-isopentyl-2,6-dimethoxy-4-methylaniline, in the form of oil. Yield: 89%.

By carrying out the preparations according to PREPARATIONS I and III, the intermediates 27 to 45 described below in TABLE B are prepared.

TABLE B

Intermediates of formula (II)

NH—R₁ on benzene with X3, X2, X1 and OCH3

| Compound | R₁ | X₁ | X₂ | X₃ | M.p.; °C. salt |
|---|---|---|---|---|---|
| 27 | —(CH₂)₄CH₃ | CH₃ | H | OCH₃ | 217, HCl |
| 28 | —(CH₂)₄CH₃ | OCH₃ | OCH₃ | H | oil |
| 29 | —(CH₂)₄CH₃ | CH₃ | OCH₃ | H | 38 |
| 30 | —(CH₂)₄CH₃ | OCH₃ | CH₃ | Cl | oil |
| 31 | —(CH₂)₄CH₃ | Cl | CH₃ | H | oil |
| 32 | —(CH₂)₄CH₃ | Cl | OCH₃ | H | 40 |
| 33 | —(CH₂)₄CH₃ | CH₃ | Cl | H | 64 |
| 34 | —(CH₂)₆—CH₃ | CH₃ | H | OCH₃ | oil |
| 35 | —(CH₂)₂CH(CH₃)₂ | OCH₃ | H | OCH₃ | 180, HCl |
| 36 | —CH₂—cyclohexyl | CH₃ | H | OCH₃ | oil |
| 37 | —(CH₂)₃OCH₃ | CH₃ | H | OCH₃ | oil |
| 38 | —CH₂CH₂—phenyl | CH₃ | H | OCH₃ | oil |
| 39 | —(CH₂)₄CH₃ | (II): Ar = 1-naphthyl | | | oil |
| 40 | —(CH₂)₄CH₃ | OCH₃ | CH₃ | H | oil |
| 41 | —(CH₂)₄CH₃ | OCH₃ | H | OCH₃ | oil |
| 42 | —(CH₂)₃CH₃ | CH₃ | H | OCH₃ | oil |
| 43 | CH₂—cyclopropyl | CH₃ | H | OCH₃ | oil |
| 44 | —CH₂—cyclopentyl | CH₃ | H | OCH₃ | oil |
| 45 | CH₃ | CH₃ | H | OCH₃ | oil |

PREPARATION IV
Compound 46—Intermediate of formula (IV)

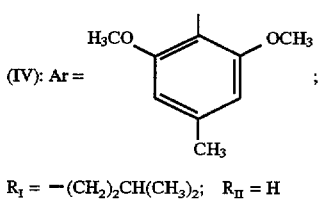

$R_I$ = —(CH₂)₂CH(CH₃)₂; $R_{II}$ = H

Synthesis with a non-chiral amino acid.

5.5 g of the aniline (compound 26) prepared above are dissolved in 60 ml of dimethylformamide. 10.8 g of BOP, 4.26 g of N-Boc-glycine and then, dropwise, 4.69 g of triethylamine are successively added to the reaction mixture and the reaction mixture is left under an inert atmosphere, at room temperature, for 20 hours. The reaction mixture is poured into 200 ml of cold water and the aqueous phase is extracted with ethyl acetate. The organic phase is washed with water and dried over anhydrous sodium sulphate. Evaporation of the solvent leaves white crystals which are purified by flash chromatography on a column of silica gel, eluent: dichloromethane/diethyl ether 95/5 (v/v) in order to obtain white crystals of N-tert-butyloxycarbonyl-[(2,6-dimethoxy-4-methylphenyl)(isopentyl)carbamoyl]methylamine; M.p.=132° C.; Yield: 91%.

PREPARATION V

Compound 47—Intermediate of formula (VIII)

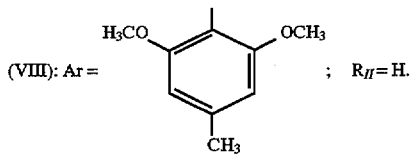

(VIII): Ar = ; R$_{II}$ = H.

Synthesis with a non-chiral amino acid.

6.6 g of N-Boc-glycine and 15.6 g of BOP are successively added to 100 ml of dimethylformamide and then, at 0° C., 14 ml of triethylamine are added dropwise. The mixture is left for 20 minutes at 0° C. and 6.7 g of 2,6-dimethoxy-4-methylaniline hydrochloride are then added portionwise. The reaction mixture is left at room temperature for 15 hours. 400 ml of ethyl acetate are added to the reaction mixture and the organic phase is successively washed with 3×200 ml of water, with a 1N aqueous sodium hydroxide solution and then with water. The organic phase is dried over anhydrous sodium sulphate. Evaporation of the solvent leaves a semi-crystalline residue which is solidified in diisopropyl ether to provide N-tert-butyloxycarbonyl-[(2,6-dimethoxy-4-methylphenyl)carbamoyl]methylamine, in the form of white crystals; M.p.=146° C.; Yield: 96%.

PREPARATION VI

Compound 48—Intermediate of formula

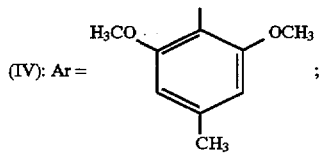

(IV): Ar = ;

R$_{II}$ = —CH$_2$CO$_2$CH$_2$C$_6$H$_5$; R$_I$ = —(CH$_2$)$_4$—CH$_3$, R enantiomer Synthesis with a chiral amino acid.

3.2 g of N-pentyl-2,6-dimethoxy-4-methylaniline (compound 27)(II) are dissolved in 50 ml of dimethylformamide and 5 g of the β-O-benzyl ester of N-Boc-aspartic acid, 7.2 g of BOP and then, dropwise, 1.6 g of N-ethylmorpholine are successively added at 0° C. and the reaction mixture is left at room temperature for 19 hours. 200 ml of ethyl acetate are then added and the organic phase is successively washed with 2×200 ml of water, 100 ml of a 0.1N aqueous sodium hydroxide solution, 100 ml of a 0.1N aqueous hydrochloric acid solution and two times 200 ml of water.

The organic phase is dried over anhydrous sodium sulphate and evaporated to dryness. The orange-coloured oil obtained is purified by filtration over a bed of silica, eluent: dichloromethane, in order to obtain benzyl3-(N-tert-butyloxycarbonyl)amino-3-{(2,6-dimethoxy-4-methylphenyl)pentylcarbamoyl}propionate in the form of an oil; Yield: 98%.

PREPARATION VII

Compound 49—Intermediate of formula (IV)

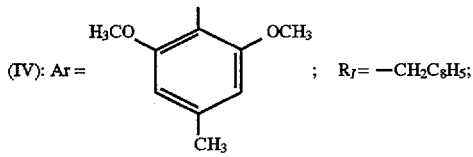

(IV): Ar = ; R$_I$= —CH$_2$C$_6$H$_5$;

R$_{II}$ = H 3.99 g of N-tert-butyloxycarbonyl-[(2,6-dimethoxy-4-methylphenyl)carbamoyl]methylamine (compound 47) are dissolved in 50 ml of dimethylformamide and 0.5 g of sodium hydride, as a 60% suspension in oil, is added portionwise at 0° C. The reaction mixture is stirred at room temperature for 30 minutes and then 2.16 g of benzyl bromide, in solution in 30 ml of dimethylformamide, are added dropwise to the reaction mixture. The reaction mixture is left at room temperature for 2 hours and then 300 ml of ethyl acetate are added. The organic phase is washed with water and dried over anhydrous sodium sulphate. Evaporation of the solvent leaves a semi-crystalline residue which is solidified in diisopropyl ether in order to obtain: N-tert-butyloxycarbonyl-[benzyl(2,6-dimethoxy-4-methylphenyl)carbamoyl]methylamine in the form of white crystals, M.p.= 163° C.; Yield: 85%.

By carrying out the preparations according to PREPARATIONS IV, VI and VII, the intermediate compounds 50 to 99 described in TABLE C below are prepared.

TABLE C

Intermediates of formula (IV)

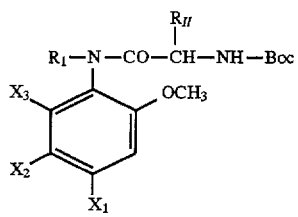

| Compound No. | $R_I$ | $R_{II}$ and configuration | $X_1$ | $X_2$ | $X_3$ | M.p.; °C. |
|---|---|---|---|---|---|---|
| 50 | —(CH$_2$)$_4$CH$_3$ | H | CH$_3$ | H | OCH$_3$ | 124 |
| 51 | —(CH$_2$)$_4$CH$_3$ | H | OCH$_3$ | CH$_3$ | Cl | oil |
| 52 | —(CH$_2$)$_4$CH$_3$ | H | OCH$_3$ | OCH$_3$ | H | 174 |
| 53 | —(CH$_2$)$_4$CH$_3$ | H | Cl | CH$_3$ | H | oil |
| 54 | —(CH$_2$)$_4$CH$_3$ | H | Cl | OCH$_3$ | H | 84 |
| 55 | —(CH$_2$)$_4$CH$_3$ | H | CH$_3$ | OCH$_3$ | H | 122 |
| 56 | —(CH$_2$)$_4$CH$_3$ | CH$_2$CH$_2$CONH$_2$ (R) | CH$_3$ | H | OCH$_3$ | oil |
| 57 | —(CH$_2$)$_4$CH$_3$ | CH$_2$CONH$_2$ (R) | CH$_3$ | H | OCH$_3$ | oil |
| 58 | —(CH$_2$)$_4$CH$_3$ | CH$_2$ (R) | CH$_3$ | H | OCH$_3$ | oil |
| 59 | —(CH$_2$)$_6$CH$_3$ | H | CH$_3$ | H | OCH$_3$ | 108 |
| 60 | —(CH$_2$)$_3$OCH$_3$ | H | CH$_3$ | H | OCH$_3$ | 135 |
| 61 | —(CH$_2$)$_2$CH(CH$_3$)$_2$ | H | OCH$_3$ | H | OCH$_3$ | oil |
| 62 | —CH$_2$-cyclohexyl | H | CH$_3$ | H | OCH$_3$ | 191 |
| 63 | —CH$_2$CH$_2$-phenyl | H | CH$_3$ | H | OCH$_3$ | 170 |
| 64 | —(CH$_2$)$_4$CH$_3$ | —CH$_2$CH$_2$COOCH$_2$-phenyl (S) | CH$_3$ | H | OCH$_3$ | oil |
| 65 | —(CH$_2$)$_4$CH$_3$ | —CH$_2$CH$_2$COOCH$_2$-phenyl (R) | CH$_3$ | H | OCH$_3$ | oil |
| 66 | —(CH$_2$)$_4$CH$_3$ | —CH$_2$-C$_6$H$_4$-O-CH$_2$-phenyl (R) | CH$_3$ | H | OCH$_3$ | oil |
| 67 | —(CH$_2$)$_4$CH$_3$ | —CH$_2$OCH$_2$-phenyl (R) | CH$_3$ | H | OCH$_3$ | 159 |

TABLE C-continued

Intermediates of formula (IV)

$$R_1-N(-CO-CH(R_{II})-NH-Boc)-Ar$$

where Ar is the substituted phenyl with $X_1$, $X_2$, $X_3$ and $OCH_3$.

| Compound No. | $R_I$ | $R_{II}$ and configuration | $X_1$ | $X_2$ | $X_3$ | M.p.; °C. |
|---|---|---|---|---|---|---|
| 68 | —(CH$_2$)$_4$CH$_3$ | —CH$_2$COOCH$_2$—Ph (R) | CH$_3$ | H | OCH$_3$ | oil |
| 69 | —(CH$_2$)$_4$CH$_3$ | —CH$_2$—Ph (R) | CH$_3$ | H | OCH$_3$ | oil |
| 70 | —(CH$_2$)$_4$CH$_3$ | H | Ar = 1-naphthyl | | | oil |
| 71 | 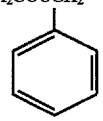 cyclohexyl | —CH$_3$ (R) | CH$_3$ | H | OCH$_3$ | oil |
| 72 | —(CH$_2$)$_4$CH$_3$ | —CH$_2$OCH$_2$—Ph (R) | OCH$_3$ | CH$_3$ | Cl | oil |
| 73 | —(CH$_2$)$_4$CH$_3$ | —CH$_2$OCH$_2$—Ph (R) | OCH$_3$ | CH$_3$ | H | oil |
| 74 | 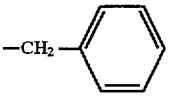 cyclooctyl | —CH$_2$OCH$_2$—Ph (R) | CH$_3$ | H | OCH$_3$ | oil |
| 75 | —(CH$_2$)$_4$CH$_3$ | —CH$_2$OCH$_2$—Ph (R) | CH$_3$ | Cl | H | oil |
| 76 | 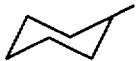 cyclohexyl | —CH$_2$OCH$_2$—Ph (R) | CH$_3$ | H | OCH$_3$ | oil |

TABLE C-continued

Intermediates of formula (IV)

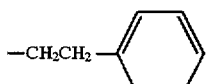

| Compound No. | $R_I$ | $R_{II}$ and configuration | $X_1$ | $X_2$ | $X_3$ | M.p.; °C. |
|---|---|---|---|---|---|---|
| 77 | —CH$_2$CH$_2$—Ph | —CH$_2$OCH$_2$—Ph (R) | CH$_3$ | H | OCH$_3$ | oil |
| 78 | —(CH$_2$)$_4$CH$_3$ | —CH$_2$OCH$_2$—Ph (R) | Cl | CH$_3$ | H | oil |
| 79 | —CH$_2$—Ph | —CH$_2$OCH$_2$—Ph (R) | CH$_3$ | H | OCH$_3$ | oil |
| 80 | —(CH$_2$)$_3$CH$_3$ | —CH$_2$OCH$_2$—Ph (R) | CH$_3$ | H | OCH$_3$ | oil |
| 81 | —(CH$_2$)$_4$CH$_3$ | —CH$_2$OCH$_2$—Ph (R) | OCH$_3$ | H | OCH$_3$ | oil |
| 82 | cyclohexyl | —CH$_2$-cyclohexyl (R) | CH$_3$ | H | OCH$_3$ | oil |
| 83 | —CH$_2$-cyclohexyl | —CH$_2$OCH$_2$—Ph (R) | CH$_3$ | H | OCH$_3$ | oil |
| 84 | —(CH$_2$)$_4$CH$_3$ | CH$_3$ (S) | CH$_3$ | H | OCH$_3$ | oil |
| 85 | —(CH$_2$)$_4$CH$_3$ | —CH$_2$-cyclohexyl (R) | CH$_3$ | H | OCH$_3$ | oil |

TABLE C-continued

Intermediates of formula (IV)

$$R_1-N(-CO-CH(R_{II})-NH-Boc)-\text{Ar}(X_3, X_2, X_1, OCH_3)$$

| Compound No. | $R_I$ | $R_{II}$ and configuration | $X_1$ | $X_2$ | $X_3$ | M.p.; °C. |
|---|---|---|---|---|---|---|
| 86 | —(CH$_2$)$_4$CH$_3$ | —CH$_2$OCH$_2$–Ph (S) | CH$_3$ | H | OCH$_3$ | oil |
| 87 | —(CH$_2$)$_4$CH$_3$ | –Ph (R, S) | CH$_3$ | H | OCH$_3$ | oil |
| 88 | —(CH$_2$)$_4$CH$_3$ | —CH(CH$_3$)$_2$ (R) | CH$_3$ | H | OCH$_3$ | oil |
| 89 | —(CH$_2$)$_4$CH$_3$ | —(CH$_2$)$_4$NHCOO—CH$_2$–Ph (R) | CH$_3$ | H | OCH$_3$ | oil |
| 90 | —(CH$_2$)$_4$CH$_3$ | —*CH(CH$_3$)O—CH$_2$–Ph (S) (R) | CH$_3$ | H | OCH$_3$ | oil |
| 91 | —(CH$_2$)$_4$CH$_3$ | —CH$_2$OCH$_2$–Ph (R) | Cl | OCH$_3$ | H | oil |
| 92 | —(CH$_2$)$_4$CH$_3$ | —CH$_2$SCH$_2$–Ph (R) | CH$_3$ | H | OCH$_3$ | oil |
| 93 | —(CH$_2$)$_4$CH$_3$ | —CH$_2$CH$_2$–Ph (R) | CH$_3$ | H | OCH$_3$ | oil |
| 94 | —CH$_2$–cyclohexyl | —CH$_2$–cyclohexyl (R) | CH$_3$ | H | OCH$_3$ | oil |

TABLE C-continued

Intermediates of formula (IV)

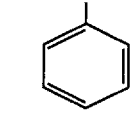

| Compound No. | $R_I$ | $R_{II}$ and configuration | $X_1$ | $X_2$ | $X_3$ | M.p.; °C. |
|---|---|---|---|---|---|---|
| 95 | —CH₂CH₃ | —CH₂OCH₂—C₆H₅ (R) | CH₃ | H | OCH₃ | oil |
| 96 | —CH₂-cyclopentyl | —CH₂OCH₂—C₆H₅ (R) | CH₃ | H | OCH₃ | oil |
| 97 | —CH₃ | —CH₂OCH₂—C₆H₅ (R) | CH₃ | H | OCH₃ | oil |
| 98 | —CH₂-cyclopropyl | —CH₂OCH₂—C₆H₅ (R) | CH₃ | H | OCH₃ | oil |
| 99 | —CH₂-cyclopropyl | —CH₂-cyclohexyl (R) | CH₃ | H | OCH₃ | oil |

PREPARATION VIII

Compound 100—Intermediate of formula (V)

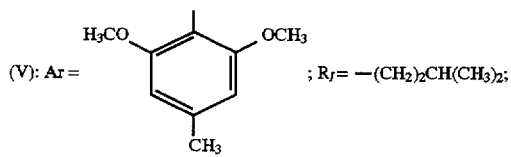

(V): Ar = ; $R_I$ = —(CH₂)₂CH(CH₃)₂;

$R_{II}$ = H.

7.8 g of N-BOC-substituted anilide (IV) (compound 46) prepared above according to PREPARATION IV are dissolved in 80 ml of ethyl acetate and cooling is carried out to 0° C. 50 ml of a saturated solution of gaseous hydrochloric acid in ethyl acetate are added to the reaction mixture and the reaction mixture is then left to return to room temperature over 2 hours. The ethyl acetate is evaporated to dryness and the semi-crystalline residue is taken up in diethyl ether. The white crystals obtained are filtered and washed with diethyl ether in order to provide white crystals of [(2,6-dimethoxy-4-methylphenyl)(isopentyl)carbamoyl]methylamine hydrochloride; M.p.=214° C.; Yield: 96%.

By carrying out the preparations according to PREPARATION VIII, the intermediate compounds 101 to 151 described in TABLE D below are prepared.

TABLE D

Intermediates of formula (V)

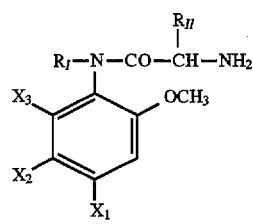

| Compound No. | $R_I$ | $R_{II}$ and configuration | $X_1$ | $X_2$ | $X_3$ | M.p.; °C. $[\alpha]_D^{20}$ (c =; solvent) |
|---|---|---|---|---|---|---|
| 101 | —(CH$_2$)$_4$CH$_3$ | H | CH$_3$ | H | OCH$_3$ | 192 |
| 102 | —(CH$_2$)$_4$CH$_3$ | H | OCH$_3$ | CH$_3$ | Cl | oil |
| 103 | —(CH$_2$)$_4$CH$_3$ | H | OCH$_3$ | OCH$_3$ | H | oil |
| 104 | —(CH$_2$)$_4$CH$_3$ | H | Cl | CH$_3$ | H | oil |
| 105 | —(CH$_2$)$_4$CH$_3$ | H | Cl | OCH$_3$ | H | oil |
| 106 | —(CH$_2$)$_4$CH$_3$ | H | CH$_3$ | OCH$_3$ | H | 161 |
| 107 | —(CH$_2$)$_4$CH$_3$ | —CH$_2$CH$_2$CONH$_2$(R) | CH$_3$ | H | OCH$_3$ | 212 ND$^{(1)}$ |
| 108 | —(CH$_2$)$_4$CH$_3$ | —CH$_2$CONH$_2$(R) | CH$_3$ | H | OCH$_3$ | 170 ND |
| 109 | —(CH$_2$)$_4$CH$_3$ | CH$_3$(R) | CH$_3$ | H | OCH$_3$ | oil ND |
| 110 | —(CH$_2$)$_6$CH$_3$ | H | CH$_3$ | H | OCH$_3$ | 169 |
| 111 | —(CH$_2$)$_3$OCH$_3$ | H | CH$_3$ | H | OCH$_3$ | 196 |
| 112 | —(CH$_2$)$_2$CH(CH$_3$)$_2$ | H | OCH$_3$ | H | OCH$_3$ | 120 HCl |
| 113 | —CH$_2$-cyclohexyl | H | CH$_3$ | H | OCH$_3$ | 207 |
| 114 | —CH$_2$-phenyl | H | CH$_3$ | H | OCH$_3$ | 190 |
| 115 | —CH$_2$CH$_2$-phenyl | H | CH$_3$ | H | OCH$_3$ | 215 |
| 116 | —(CH$_2$)$_4$CH$_3$ | —CH$_2$CH$_2$COOCH$_2$-phenyl (S) | CH$_3$ | H | OCH$_3$ | oil ND |
| 17 | —(CH$_2$)$_4$CH$_3$ | —CH$_2$CH$_2$COOCH$_2$-phenyl (R) | CH$_3$ | H | OCH$_3$ | oil ND |
| 118 | —(CH$_2$)$_4$CH$_3$ | —CH$_2$-(4-benzyloxyphenyl) (R) | CH$_3$ | H | OCH$_3$ | 90 ND |

TABLE D-continued

Intermediates of formula (V)

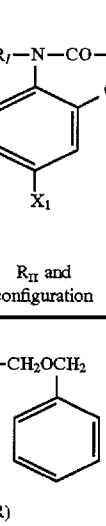

| Compound No. | $R_I$ | $R_{II}$ and configuration | $X_1$ | $X_2$ | $X_3$ | M.p.; °C. $[\alpha]_D^{20}$ (c =; solvent) |
|---|---|---|---|---|---|---|
| 119 | —(CH$_2$)$_4$CH$_3$ | —CH$_2$OCH$_2$-Ph (R) | CH$_3$ | H | OCH$_3$ | oil ND |
| 120 | —(CH$_2$)$_4$CH$_3$ | —CH$_2$COOCH$_2$-Ph (R) | CH$_3$ | H | OCH$_3$ | oil ND |
| 121 | —(CH$_2$)$_4$CH$_3$ | —CH$_2$-Ph (R) | CH$_3$ | H | OCH$_3$ | oil ND |
| 122 | —(CH$_2$)$_4$CH$_3$ | H | Ar = 1-naphthyl | | | 85 |
| 123 | 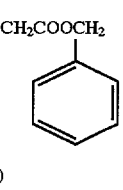 | —CH$_3$(R) | CH$_3$ | H | OCH$_3$ | oil ND |
| 124 | —(CH$_2$)$_4$CH$_3$ | —CH$_2$OCH$_2$-Ph (R) | OCH$_3$ | CH$_3$ | Cl | oil −112.0 (1; CH$_3$OH) |
| 125 | —(CH$_2$)$_4$CH$_3$ | —CH$_2$OCH$_2$-Ph (R) | OCH$_3$ | CH$_3$ | H | oil −3.7 (0.8; CH$_3$OH) |
| 126 | 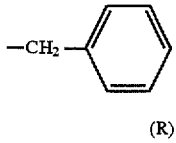 | —CH$_2$OCH$_2$-Ph (R) | CH$_3$ | H | OCH$_3$ | oil ND |

TABLE D-continued

Intermediates of formula (V)

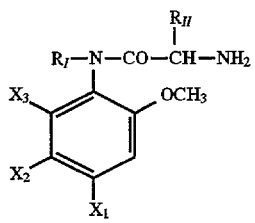

| Compound No. | $R_I$ | $R_{II}$ and configuration | $X_1$ | $X_2$ | $X_3$ | M.p.; °C. $[\alpha]_D^{20}$ (c =; solvent) |
|---|---|---|---|---|---|---|
| 127 | —(CH$_2$)$_4$CH$_3$ | —CH$_2$OCH$_2$—C$_6$H$_5$ (R) | CH$_3$ | Cl | H | oil<br>ND |
| 128 | cyclohexyl | —CH$_2$OCH$_2$—C$_6$H$_5$ (R) | CH$_3$ | H | OCH$_3$ | oil<br>−3.0<br>(1; CH$_3$OH) |
| 129 | —CH$_2$CH$_2$—C$_6$H$_5$ | —CH$_2$OCH$_2$—C$_6$H$_5$ (R) | CH$_3$ | H | OCH$_3$ | oil<br>−25.7<br>(1.4; CH$_3$OH) |
| 130 | —(CH$_2$)$_4$CH$_3$ | —CH$_2$OCH$_2$—C$_6$H$_5$ (R) | Cl | CH$_3$ | H | oil<br>+81.0<br>(1.65; CH$_3$OH) |
| 131 | —CH$_2$—C$_6$H$_5$ | —CH$_2$OCH$_2$—C$_6$H$_5$ (R) | CH$_3$ | H | OCH$_3$ | oil<br>ND |
| 132 | —(CH$_2$)$_3$CH$_3$ | —CH$_2$OCH$_2$—C$_6$H$_5$ (R) | CH$_3$ | H | OCH$_3$ | oil<br>ND |
| 133 | —(CH$_2$)$_4$CH$_3$ | —CH$_2$OCH$_2$—C$_6$H$_5$ (R) | OCH$_3$ | H | OCH$_3$ | oil<br>−22.1<br>(1; CH$_3$OH) |

TABLE D-continued

Intermediates of formula (V)

| Compound No. | $R_I$ | $R_{II}$ and configuration | $X_1$ | $X_2$ | $X_3$ | M.p.; °C. $[\alpha]_D^{20}$ (c =; solvent) |
|---|---|---|---|---|---|---|
| 134 | cyclohexyl | —CH₂—cyclohexyl (R) | CH₃ | H | OCH₃ | oil −10.9 (1.15; CH₃OH) |
| 135 | —CH₂—cyclohexyl | —CH₂OCH₂—phenyl (R) | CH₃ | H | OCH₃ | oil +16.0 (0.65; CH₃OH) |
| 136 | —(CH₂)₄CH₃ | —CH₃ (S) | CH₃ | H | OCH₃ | oil ND |
| 137 | —(CH₂)₄CH₃ | —CH₂—cyclohexyl (R) | CH₃ | H | OCH₃ | oil −33.0 (1.17; CH₃OH) |
| 138 | —(CH₂)₄CH₃ | —CH₂OCH₂—phenyl (S) | CH₃ | H | OCH₃ | oil −174.0 (1.07; CH₃OH) |
| 139 | —(CH₂)₄CH₃ | —phenyl (R, S) | CH₃ | H | OCH₃ | oil |
| 140 | —(CH₂)₄CH₃ | —CH(CH₃)₂ (R) | CH₃ | H | OCH₃ | oil −28.0 (1; CH₃OH) |
| 141 | —(CH₂)₄CH₃ | —(CH₂)₄NHCOO—CH₂—phenyl (R) | CH₃ | H | OCH₃ | oil −32.0 (1: CH₂Cl₂) |
| 142 | —(CH₂)₄CH₃ | —CH(CH₃)O—CH₂—phenyl (R) | CH₃ | H | OCH₃ | oil ND |

TABLE D-continued

Intermediates of formula (V)

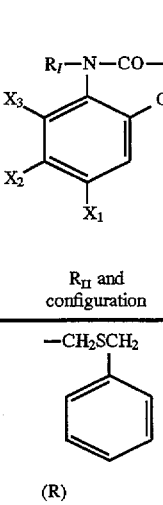

| Compound No. | $R_I$ | $R_{II}$ and configuration | $X_1$ | $X_2$ | $X_3$ | M.p.; °C. $[\alpha]_D^{20}$ (c =; solvent) |
|---|---|---|---|---|---|---|
| 143 | —(CH$_2$)$_4$CH$_3$ | —CH$_2$SCH$_2$—C$_6$H$_5$ (R) | CH$_3$ | H | OCH$_3$ | oil −21.2 (1; CH$_3$OH) |
| 144 | —(CH$_2$)$_4$CH$_3$ | —CH$_2$CH$_2$—C$_6$H$_5$ (R) | CH$_3$ | H | OCH$_3$ | oil ND |
| 145 | —CH$_2$—cyclohexyl | —CH$_2$—cyclohexyl (R) | CH$_3$ | H | OCH$_3$ | 148° C. (hydrochloride) −21.7 (1.05; CH$_3$OH) |
| 146 | —(CH$_2$)$_4$CH$_3$ | —CH$_2$OCH$_2$—C$_6$H$_5$ (R) | Cl | OCH$_3$ | H | oil −5.4 (1.45; CH$_3$OH) |
| 147 | —(CH$_2$CH$_3$ | —CH$_2$OCH$_2$—C$_6$H$_5$ (R) | CH$_3$ | H | OCH$_3$ | oil −25.0 (1.15; CH$_3$OH) |
| 148 | —CH$_2$—cyclopentyl | —CH$_2$OCH$_2$—C$_6$H$_5$ (R) | CH$_3$ | H | OCH$_3$ | OIL −47.9 (1; CH$_3$OH) |
| 149 | —CH$_2$—cyclopropyl | —CH$_2$—cyclohexyl (R) | CH$_3$ | H | OCH$_3$ | oil −17.9 (1; CH$_3$OH) |
| 150 | CH$_3$ | —CH$_2$OCH$_2$—C$_6$H$_5$ (R) | CH$_3$ | H | OCH$_3$ | oil −13.5 (1; CH$_3$OH) |

TABLE D-continued

Intermediates of formula (V)

$$R_I-N(-CO-CH(-R_{II})-NH_2)-\text{Ar}(X_3, X_2, X_1, OCH_3)$$

| Compound No. | $R_I$ | $R_{II}$ and configuration | $X_1$ | $X_2$ | $X_3$ | M.p.; °C. $[\alpha]_D^{20}$ (c =; solvent) |
|---|---|---|---|---|---|---|
| 151 | —CH$_2$—cyclopropyl | —CH$_2$OCH$_2$—Ph (R) | CH$_3$ | H | OCH$_3$ | oil −30.8 (1; CH$_3$OH) |

(1): ND: $[\alpha]_D$ not determined

EXAMPLE 1

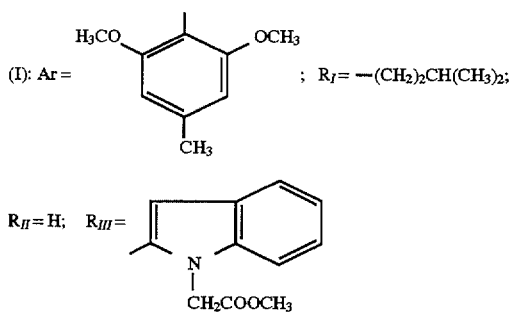

(I): Ar = 2,6-dimethoxy-4-methylphenyl; $R_I$ = —(CH$_2$)$_2$CH(CH$_3$)$_2$;
$R_{II}$=H; $R_{III}$ = 1-(CH$_2$COOCH$_3$)-indol-2-yl 0.8 9 of [(2,6-dimethoxy-4-methylphenyl)(isopentyl)carbamoyl]methylamine hydrochloride (compound 100) is dissolved in 10 ml of dimethylformamide and 0.58 g of 1-(methoxycarbonylmethyl)-2-indolecarboxylic acid, 1.12 g of BOP and then, dropwise, 0.75 g of triethylamine are successively added to the reaction mixture at room temperature. The reaction mixture is left at room temperature for 20 hours, is then poured into cold water and the aqueous phase is extracted with ethyl acetate. The organic extracts are washed with water and then dried over anhydrous sodium sulphate. Evaporation of the solvent leaves a yellow oil which is purified by flash chromatography on a column of silica gel, eluent: dichloromethane/methanol 98/2 (v/v) in order to obtain white crystals of methyl{2-[[(2,6-dimethoxy-4-methylphenyl)(isopentyl)carbamoyl]methylcarbamoyl]-1-indolyl}acetate; M.p.=141° C.; Yield: 91%.

EXAMPLE 2

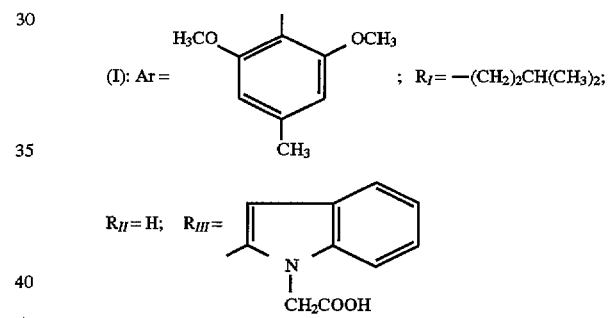

(I): Ar = 2,6-dimethoxy-4-methylphenyl; $R_I$ = —(CH$_2$)$_2$CH(CH$_3$)$_2$;
$R_{II}$=H; $R_{III}$ = 1-(CH$_2$COOH)-indol-2-yl 0.6 g of the ester prepared according to EXAMPLE 1 is suspended in 20 ml of methanol and 1.8 ml of a 1N aqueous sodium hydroxide solution are added to the reaction mixture. 6 ml of dimethylformamide are added in order to homogenize the reaction mixture and the reaction mixture is then left for 2 hours at room temperature. The methanol is evaporated and the residue is poured into cold water. The aqueous phase is acidified with a 1N aqueous hydrochloric acid solution and extracted with dichloromethane. The organic extracts are washed with water and dried over anhydrous sodium sulphate. Evaporation of the solvent leaves white crystals of {2-[[(2,6-dimethoxy-4-methylphenyl)(isopentyl)carbomoyl]methylcarbomyl]-1-indolyl}acetic acid, which are washed with diisopropyl ether, M.p.=208° C.; Yield: 96%.

EXAMPLE 3

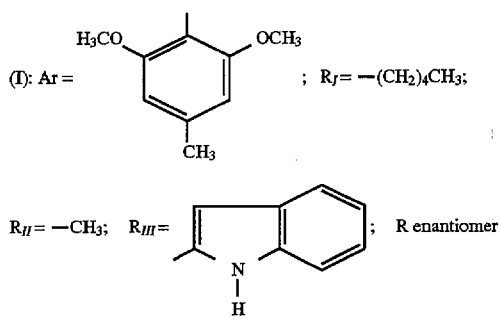

(I): Ar = [2,6-dimethoxy-4-methylphenyl] ; R_I = —(CH_2)_4CH_3;

R_II = —CH_3; R_III = [indol-2-yl] ; R enantiomer 0.6 g of (R)-2-[(2,6-dimethoxy-4-methylphenyl) pentylcarbamoyl]ethylamine hydrochloride (compound 109) is suspended in 10 ml of dimethylformamide. 0.286 g of 1H-indole-2-carboxylic acid, 0.808 g of BOP and, dropwise, 0.6 g of N-ethylmorpholine are added at 0° C. and the reaction mixture is left at room temperature for 18 hours. The reaction mixture is poured into cold water and the aqeuous phase is extracted with ethyl acetate. The organic extracts are washed with water and dried over anhydrous sodium sulphate. Evaporation of the solvent leaves a brown crystalline residue which is purified by chromatography on a column of silica gel, eluent: dichloromethane/ethanol 99/1 (v/v) in order to obtain (R)-N-{1-[(2,6-dimethoxy-4-methylphenyl)pentylcarbomoyl]ethyl}-1H-indole-2-carboxamide, in the form of white crystals; M.p.=193° C.; Yield: 84% $[\alpha]_D^{20} = -78°$ (c=1, $CH_2Cl_2$).

EXAMPLE 4

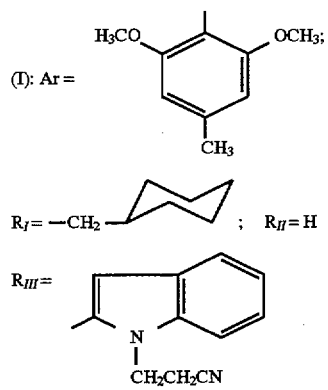

(I): Ar = [2,6-dimethoxy-4-methylphenyl]

R_I = —CH_2—[cyclohexyl] ; R_II = H

R_III = [1-(2-cyanoethyl)indol-2-yl] ; CH_2CH_2CN 1.5 g of [(cyclohexylmethyl)(2,6-dimethoxy-4-methylphenyl)carbamoyl]methylamine hydrochloride (compound 113) are dissolved in 10 ml of dimethylformamide and 0.918 g of 1-(2-cyanoethyl)-2-indolecarboxylic acid, 1.95 g of BOP and then, dropwise, 1.28 g of triethylamine are then successively added. The reaction mixture is left at room temperature for 3 hours, is then poured into cold water and the aqueous phase is extracted with ethyl acetate. The organic extracts are dried over anhydrous sodium sulphate and evaporated to dryness. The residue is purified by flash chromatography on a column of silica gel, eluent: dichloromethane/methanol 98/2 (v/v) in order to obtain 3-{2-[[(cyclohexylmethyl)(2,6-dimethoxy-4-methylphenyl) carbamoyl]methylcarbamoyl]-1-indolyl}propionitrile in the form of a pasty foam; Yield: 91%.

EXAMPLE 5

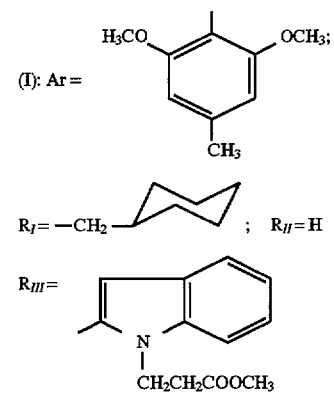

(I): Ar = [2,6-dimethoxy-4-methylphenyl]

R_I = —CH_2—[cyclohexyl] ; R_II = H

R_III = [1-(CH_2CH_2COOCH_3)indol-2-yl]

40 ml of methanol are saturated at 0° C. (duration 30 minutes) with gaseous hydrochloric acid. 1.9 g of the nitrile prepared according to EXAMPLE 4, dissolved beforehand in 10 ml of methanol and cooled to −10° C., are introduced dropwise therein and the reaction mixture is left at −5° C. for 18 hours. Degasing is carried out and then the methanol is evaporated to dryness. The residue is taken up in a mixture of water and methanol and the reaction mixture is left at room temperature for 3 hours. Evaporation is carried out to dryness and the residue is taken up in water. The aqueous phase is extracted with ethyl acetate. The organic extracts are dried over anhydrous sodium sulphate and evaporated under vacuum to dryness. The oily residue is purified by chromatography on a column of silica gel, eluent: dichloromethane/methanol 98/2 (v/v) in order to obtain white crystals of methyl 3-{2-[[(cyclohexylmethyl)(2,6-dimethoxy-4-methylphenyl)carbamoyl]methylcarbamoyl]-1-indolyl}propionate; M.p.=68° C.; Yield: 92%.

EXAMPLE 6

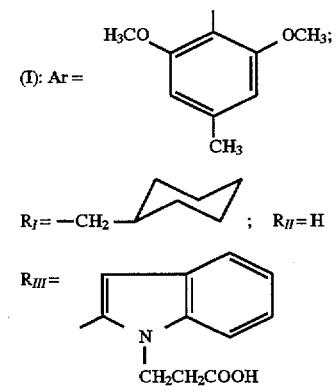

(I): Ar = [2,6-dimethoxy-4-methylphenyl]

R_I = —CH_2—[cyclohexyl] ; R_II = H

R_III = [1-(CH_2CH_2COOH)indol-2-yl]

1.2 g of the ester prepared above according to EXAMPLE 5 are dissolved in 15 ml of methanol and 3.4 ml of a 1N lithium hydroxide solution are added. The reaction mixture is left at room temperature for 18 hours, the methanol is then evaporated and the residue is taken up in water. The aqueous phase is extracted with ethyl acetate. The organic extracts are dried over anhydrous sodium sulphate and evaporated to dryness. The colourless oil is crystallized from pentane in order to provide white crystals of 3-{2-[[(cyclohexylmethyl) (2,6-dimethoxy-4-methylphenyl)carbamoyl] methylcarbamoyl]-1-indolyl}propionic acid; M.p.=110° C.; Yield: 98%.

EXAMPLE 7

(I): Ar = 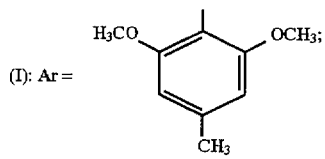

$R_I$ = —CH₂—  ; $R_{II}$ = H;

$R_{III}$ = 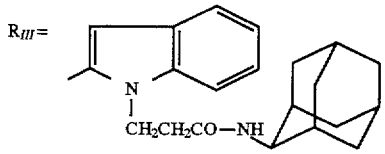

0.6 g of the acid prepared according to EXAMPLE 6 is dissolved in 10 ml of dimethylformamide and then 0.173 g of 2-adamantanamine, 0.505 g of BOP and then, dropwise, 0.227 g of triethylamine are added to the reaction mixture. The reaction mixture is left at room temperature for 18 hours, is then poured into water and the aqueous phase is extracted with ethyl acetate. The organic extracts are dried over anhydrous sodium sulphate and evaporated to dryness. The residue obtained is purified by chromatography on a column of silica gel, eluent dichloromethane/methanol 99/1 (v/v).

White crystals of N-(2-adamantyl)-3-[2-{[(cyclohexylmethyl)(2,6-dimethoxy-4-methylphenyl)carbamoyl]methylcarbamoyl}-1-indolyl]propionamide are obtained; M.p.=96° C.; Yield: 88%.

By carrying out the preparations according to EXAMPLES 1 to 7 and by using the appropriate starting products, EXAMPLES 8 to 184 described in TABLES I to VII below are prepared.

TABLE I

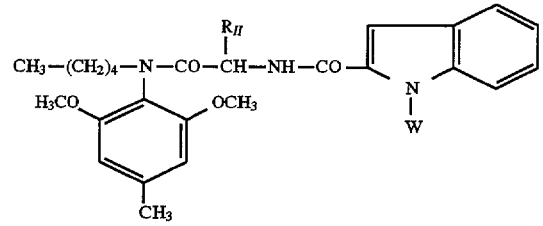

| Example Number | $R_{II}$ and configuration | W | M.p.; °C. | $[\alpha]^{20}_D$ (c = ; solvent) |
|---|---|---|---|---|
| 8 | H | H | 180 | — |
| 9 | H | —CH₂COOCH₃ | 130 | — |
| 10 | H | —CH₂COOH | 188 | — |
| 11 | H | —CH₂CH₂COOH | 76 | — |
| 12 | —CH₃ (R) | —CH₂COOCH₃ | 73 | ND |
| 13 | —CH₃ (R) | —CH₂COOH | 98 | −99.6 (1; CH₃OH) |
| 14 | —CH₂OH (R) | H | 124 | −48.4 (1; CH₂Cl₂) |
| 15 | —CH₂COOH (R) | H | 205 | −76.8 (1; CHCl₃) |
| 16 | —CH₂CH₂COOH (R) | H | 110 | −84.6 (0.9; DMF) |
| 17 | —CH₂CH₂COOH (S) | H | 110 | +67.6 (0.9; DMF) |
| 18 | —CH₂—⌬ (R) | H | 252 | −12.7 (1.05; CH₂Cl₂) |
| 19 | —CH₂—⌬—OH (R) | H | 204 | −8.8 (0.99; DMF) |

TABLE I-continued

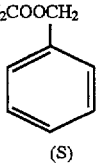

| Example Number | $R_{II}$ and configuration | W | M.p.; °C. | $[\alpha]^{20}_D$ (c = ; solvent) |
|---|---|---|---|---|
| 20 | —CH₂CH₂COOCH₂—C₆H₅ (S) | H | 124 | +57.0 (1; DMF) |
| 21 | —CH₂CH₂COOCH₂—C₆H₅ (R) | H | 128 | −56.2 (1; DMF) |
| 22 | —CH₂OCH₂—C₆H₅ (R) | H | 179 | −62.2 (1; CH₂Cl₂) |
| 23 | —CH₂CONH₂ (R) | H | 206 | insoluble |
| 24 | —CH₂CH₂CONH₂ (R) | H | 135 | −99.8 (1.04; CH₂Cl₂) |
| 25 | —CH₂—C₆H₄—O—CH₂—C₆H₅ (R) | H | 193 | ND |
| 26 | —CH₂OH (R) | —CH₂COOH | 192 | −36.6 (1; CH₃OH) |
| 27 | —CH₂COOH (R) | —CH₂COOH | 115 | −85.0 (1, CHCl₃) |
| 28 | —CH₂CH₂COOH (R) | —CH₂COOH | 100 | −67.7 (0.9; DMF) |
| 29 | —CH₂CH₂COOH (S) | —CH₂COOH | 128 | +73.3 (0.9; DMF) |
| 30 | —CH₂—C₆H₅ (R) | —CH₂COOH | 115 | −25.6 (1.02; CH₃OH) |

TABLE I-continued

Structure: CH₃—(CH₂)₄—N(—C₆H₂(OCH₃)₂CH₃)—CO—CH(R$_{II}$)—NH—CO—(indole-2-yl, N-W)

| Example Number | R$_{II}$ and configuration | W | M.p. °C. | [α]$^{20}_D$ (c = ; solvent) |
|---|---|---|---|---|
| 31 | —CH₂—C₆H₄—OH (R) | —CH₂COOH | 238 | −8.3 (1.02; DMF) |
| 32 | —CH₂CONH₂ (R) | —CH₂COOH | 150 | −62.7 (1; CH₃OH) |
| 33 | —CH₂CH₂CONH₂ (R) | —CH₂COOH | 150 | −106.4 (1.17; CH₂Cl₂) |
| 34 | —CH₂OH (R) | —CH₂COOCH₃ | 87 | −62.2 (1; CH₃OH) |
| 35 | —CH₂COOH (R) | —CH₂COO—CH₃ | 104 | −81.0 (0.99; CHCl₃) |
| 36 | —CH₂CH₂COOH (R) | —CH₂COOCH₃ | 80 | −62.4 (0.9; DMF) |
| 37 | —CH₂—C₆H₅ (R) | —CH₂COOCH₃ | 162 | −21.8 (CH₃OH) |
| 38 | —CH₂—C₆H₄—OH (R) | —CH₂COOCH₃ | 120 | −10.6 (0.98; DMF) |
| 39 | —CH₂CH₂COOCH₂—C₆H₅ (R) | —CH₂COOCH₃ | 50 | −47.3 (0.9; DMF) |
| 40 | —CH₂CH₂COOCH₂—C₆H₅ (S) | —CH₂COOCH₃ | 48 | +47.0 (0.9; DMF) |
| 41 | —CH₂CONH₂ (R) | —CH₂COOCH₃ | 213 | −115.2 (1; CH₂Cl₂) |
| 42 | —CH₂CH₂CONH₂ (R) | —CH₂COOCH₃ | 152 | −80.8 (1.02; CH₂Cl₂) |
| 43 | —CH₂COOCH₂—C₆H₅ (R) | tetrahydropyran-2-yl | 66 | −51.8 (1; CHCl₃) |

TABLE I-continued $CH_3-(CH_2)_4-N-CO-CH(R_{II})-NH-CO-$[indole-2-yl, N-W]; phenyl has $H_3CO$, $OCH_3$ (2,6) and $CH_3$ (4)

| Example Number | $R_{II}$ and configuration | W | M.p. °C. | $[\alpha]^{20}_D$ (c = ; solvent) |
|---|---|---|---|---|
| 44 | —CH$_2$OC$_6$H$_5$ (R) | —CH$_2$COONa | 154 | −35.8 (0.92; CH$_3$OH) |
| 45 | —CH$_3$ (S) | —CH$_2$COOCH$_3$ | 72 | +101.5 (1; CH$_3$OH) |
| 46 | —CH$_3$ (S) | —CH$_2$COOH | 94 | +100.8 (1; CH$_3$OH) |
| 47 | —CH$_3$ (S) | H | 195 | +86.3 (1; CH$_2$Cl$_2$) |
| 48 | —CH$_3$ (R) | —CH$_2$CON(piperidyl) | 86 | −81.5 (0.998; CH$_3$OH) |
| 49 | —CH$_2$-cyclohexyl (R) | H | 242 | −29.7 (0.96; CH$_2$Cl$_2$) |
| 50 | —CH$_2$-cyclohexyl (R) | —CH$_2$COOCH$_3$ | 90 | −62.2 (1.1; CH$_2$Cl$_2$) |
| 51 | —CH$_2$-cyclohexyl (R) | —CH$_2$COONa | 220 | −40.2 (0.96; CH$_2$Cl$_2$) |
| 52 | —CH$_2$OC$_6$H$_5$ (S) | —CH$_2$COOCH$_3$ | 60 | +47.2 (0.94; CH$_3$OH) |
| 53 | —CH$_2$OC$_6$H$_5$ (S) | H | 176 | +47.8 (0.93; CH$_2$Cl$_2$) |
| 54 | —CH$_3$ (R) | —CH$_2$CH$_2$COOH | 67 | −102.9 (0.998; CH$_3$OH) |
| 55 | —CH$_3$ (R) | —CH$_3$ | 67 | −114.0 (1; CH$_3$OH) |
| 56 | —CH$_2$OC$_6$H$_5$ (S) | —CH$_2$COOLi | 158 | +40.0 (1; CH$_3$OH) |

TABLE I-continued

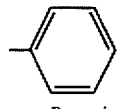

| Example Number | $R_{II}$ and configuration | W | M.p.; °C. | $[\alpha]^{20}_D$ (c = ; solvent) |
|---|---|---|---|---|
| 57 | —CH₃ (R) | —CH₂CH₂OH | 66 | −108.9 (1; CH₃OH) |
| 58 | —CH₃ (R) | —CH₂COOCH₃ | 60 | −46.5 (1.1; CH₃OH) |
| 59 | 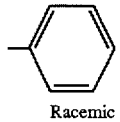 Racemic | —CH₂COOCH₃ | 75 | — |
| 60 | 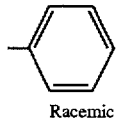 Racemic | H | 229 | — |
| 61 | 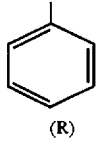 Racemic | —CH₂COOH | 186 | — |
| 62 | —CH₃ (R) | —C₂H₅ | 48 | −116.2 (1.005; CH₃OH) |
| 63 | —CH(CH₃)₂ (R) | H | 231 | −148.1 (1; DMF) |
| 64 | —CH(CH₃)₂ (R) | —CH₂COOCH₃ | 76 | −102.5 (1; CH₃OH) |
| 65 | —CH(CH₃)₂ (R) | —CH₂COOH | 192 | −113.4 (1; CH₃OH) |
| 66 | —(CH₂)₄NHCOOCH₂  (R) | —CH₂COOCH₃ | 68 | −44.0 (1; CH₃OH) |
| 67 | —(CH₂)₄NHCOOCH₂  (R) | H | 95 | −63.3 (0.92; CH₃OH) |
| 68 | —(CH₂)₄NH₂ (R) | H | 134 | −83,9 (0,9; CH₃OH) |
| 69 | —(CH₂)₄NHCOOCH₂ (R) | —CH₂COOH | 118 | −46,5 (1; CH₃OH) |

TABLE I-continued

[Structure: CH₃—(CH₂)₄—N(Ar)—CO—CH(R_II)—NH—CO—(indole-2-yl with N-W); Ar = 2,6-dimethoxy-4-methylphenyl]

| Example Number | R_II and configuration | W | M.p. °C. | $[\alpha]^{20}_D$ (c = ; solvent) |
|---|---|---|---|---|
| 70 | —CH₂OCH₂—C₆H₅ (R) | —CH₂CH₂COOCH₃ | huile | −46,7 (0,8; CH₃OH) |
| 71 | —CH₂OCH₂—C₆H₅ (R) | —CH₂CH₂COOH | 84 | −45,0 (0,85; CH₃OH) |
| 72 | —*CH(CH₃)O—CH₂—C₆H₅ (S)(R) | —CH₂COOCH₃ | 117 | −95,0 (0,995; CH₃OH) |
| 73 | —*CH(CH₃)O—CH₂—C₆H₅ (S)(R) | —CH₂COOH | 85 | −100,7 (1,01; CH₃OH) |
| 74 | —*CH(CH₃)O—CH₂—C₆H₅ (S)(R) | H | 195 | −92.5 (1; CH₂Cl₂) |
| 75 | —(CH₂)₄NH₂ (R) | —CH₂COOH | 173 | −173.0 (0.6; CH₃OH) |
| 76 | —CH₂OCH₂—C₆H₅ (R) | —CH₂CH₃ | oil | −48.3 (1; CH₃OH) |
| 77 | —CH₂OCH₂—C₆H₅ (R) | —CH₃ | 107 | −60.4 (1; CH₃OH) |

TABLE I-continued

Structure: CH₃—(CH₂)₄—N(Ar)—CO—CH(R$_{II}$)—NH—CO—(indole-2-yl with N-W), where Ar = 2,6-dimethoxy-4-methylphenyl

| Example Number | R$_{II}$ and configuration | W | M.p.; °C. | $[\alpha]^{20}_D$ (c = ; solvent) |
|---|---|---|---|---|
| 78 | —CH₂SCH₂—C₆H₅ (R) | —CH₂COOCH₃ | 110 | −23.7 (1.007; CH₃OH) |
| 79 | —CH₂CH₂—C₆H₅ (R) | —CH₂COOCH₃ | 66 | −32.6 (0.995; CH₃OH) |
| 80 | —CH₂OCH₂—C₆H₅ (R) | —CH₂CH₂OH | 58 | −32.4 (1; CH₃OH) |
| 81 | —CH₂SCH₂—C₆H₅ (R) | —CH₂COOH | 72 | −20.6 (1; CH₃OH) |
| 82 | —CH₂CH₂—C₆H₅ (R) | —CH₂COOH | 101 | −34.0 (1; CH₃OH) |

TABLE II

Structure: CH₃—(CH₂)₄—N(Ar)—CO—CH₂—NH—CO—(indole-2-yl with N-W), where Ar has substituents X₁ (para), X₂ (meta), X₃ (ortho), and OCH₃ (other ortho).

| Example Number | X₁ | X₂ | X₃ | W | M.p.; °C. |
|---|---|---|---|---|---|
| 83 | OCH₃ | CH₃ | Cl | —CH₂COOCH₃ | 129 |
| 84 | OCH₃ | CH₃ | Cl | H | 178 |
| 85 | OCH₃ | CH₃ | Cl | CH₂COOH | 175 |
| 86 | Cl | CH₃ | H | CH₂COOCH₃ | 90 |
| 87 | Cl | CH₃ | H | H | 189 |
| 88 | Cl | CH₃ | H | —CH₂COOH | 197 |
| 89 | Cl | OCH₃ | H | H | 194 |
| 90 | Cl | OCH₃ | H | —CH₂COOCH₃ | 132 |
| 91 | Cl | OCH₃ | H | —CH₂COOH | 118 |
| 92 | CH₃ | Cl | H | H | 196 |

TABLE II-continued

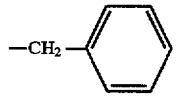

| Example Number | $X_1$ | $X_2$ | $X_3$ | W | M.p.; °C. |
|---|---|---|---|---|---|
| 93 | $CH_3$ | Cl | H | $-CH_2COOCH_3$ | 116 |
| 94 | $CH_3$ | Cl | H | $-CH_2-COO^-Na^+$ | 115 |

TABLE III

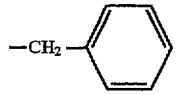

| Example Number | $X_1$ | $X_2$ | W | M.p.; °C. |
|---|---|---|---|---|
| 95 | $OCH_3$ | $CH_3$ | H | 61 |
| 96 | $OCH_3$ | $CH_3$ | $CH_2COOH$ | 130 |
| 97 | $CH_3$ | $OCH_3$ | H | 189 |
| 98 | $OCH_3$ | $OCH_3$ | $CH_2COOCH_3$ | 51 |
| 99 | $OCH_3$ | $OCH_3$ | $CH_2COOH$ | 202 |
| 100 | $OCH_3$ | $OCH_3$ | H | 199 |
| 101 | $CH_3$ | $OCH_3$ | $CH_2COOCH_3$ | 110 |
| 102 | $CH_3$ | $OCH_3$ | tetrahydropyran-2-yl | 76 |
| 103 | $CH_3$ | $OCH_3$ | $CH_2COOH$ | 166 |

TABLE IV

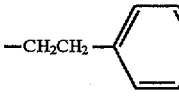

| Example Number | $R_I$ | W | $X_1$ | $X_2$ | M.p.; °C. |
|---|---|---|---|---|---|
| 104 | $-(CH_2)_6CH_3$ | H | $CH_3$ | $OCH_3$ | 129 |
| 105 | $-(CH_2)_6CH_3$ | $-CH_2COOH$ | $CH_3$ | $OCH_3$ | 178 |
| 106 | $-(CH_2)_6CH_3$ | $-(CH_2)_2COOCH_3$ | $CH_3$ | $OCH_3$ | 91 |
| 107 | $-(CH_2)_6CH_3$ | $-(CH_2)_2COOH$ | $CH_3$ | $OCH_3$ | 85 |
| 108 | $-(CH_2)_2CH(CH_3)_2$ | H | $CH_3$ | $OCH_3$ | 199 |
| 109 | $-(CH_2)_2CH(CH_3)_2$ | H | $OCH_3$ | $OCH_3$ | 188 |
| 110 | $-(CH_2)_2CH(CH_3)_2$ | $-CH_2COOH$ | $OCH_3$ | $OCH_3$ | 226 |
| 111 | $-CH_2-C_6H_5$ | H | $CH_3$ | $OCH_3$ | 225 |
| 112 | $-CH_2-C_6H_5$ | $-CH_2COO^-Na^+$ | $CH_3$ | $OCH_3$ | 235 |
| 113 | $-CH_2CH_2-C_6H_5$ | H | $CH_3$ | $OCH_3$ | 238 |
| 114 | $-CH_2CH_2-C_6H_5$ | $-CH_2COOCH_3$ | $OCH_3$ | H | 163 |

TABLE IV-continued

Structure: $R_I-N(C(=O)-CH_2-NH-C(=O)-\text{indol-2-yl}(N-W))-\text{aryl}$ where aryl has OCH₃ (ortho), X₂ (ortho), X₁ (para)

| Example Number | R$_I$ | W | X$_1$ | X$_2$ | M.p.; °C. |
|---|---|---|---|---|---|
| 115 | —CH₂CH₂—phenyl | —CH₂COOH | OCH₃ | H | 198 |
| 116 | —CH₂—cyclohexyl | H | CH₃ | OCH₃ | 234 |
| 117 | —CH₂—cyclohexyl | —CH₂COOCH₃ | CH₃ | OCH₃ | 161 |
| 118 | —CH₂—cyclohexyl | —CH₂COOH | CH₃ | OCH₃ | 212 |
| 119 | —CH₂—cyclohexyl | —CH₂CONH—2-Ada (1) | CH₃ | OCH₃ | 196 |
| 120 | —(CH₂)₃OCH₃ | H | CH₃ | OCH₃ | 198 |
| 121 | —(CH₂)₃OCH₃ | —CH₂COOH | CH₃ | OCH₃ | 202 |
| 122 | —(CH₂)₃OCH₃ | —CH₂COOCH₃ | CH₃ | OCH₃ | 76 |
| 123 | —(CH₂)₃OCH₃ | —(CH₂)₂COOH | CH₃ | OCH₃ | 103 |
| 124 | —(CH₂)₃OCH₃ | —(CH₂)₂COOCH₃ | CH₃ | OCH₃ | 94 |
| 125 | —(CH₂)₂CH(CH₃)₂ | —CH₂COOH | OCH₃ | OCH₃ | 226 |

Note: (1) 2-ada represents the 2-adamantyl group

TABLE V

Structure: $R_I-N(C(=O)-CH_2-NH-C(=O)-R_{III})$-aryl, aryl = 2,6-dimethoxy-4-methylphenyl

| Example Number | R$_I$ | R$_{III}$ | M.p.; °C. |
|---|---|---|---|
| 126 | —(CH₂)₄CH₃ | 2-naphthyl | 136 |
| 127 | —(CH₂)₄CH₃ | 3-quinolyl | 173 |
| 128 | —(CH₂)₄CH₃ | 2-methylquinolin-?-yl | 173 |
| 129 | —(CH₂)₆CH₃ | 2-naphthyl | 108 |
| 130 | —(CH₂)₆CH₃ | isoquinolin-3-yl | 150 |

TABLE V-continued

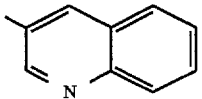

| Example Number | $R_I$ | $R_{III}$ | M.p.; °C. |
|---|---|---|---|
| 131 | —(CH₂)₆CH₃ | 3-quinolinyl | 98 |
| 132 | —(CH₂)₆CH₃ | 2-methyl-quinolinyl | 122 |
| 133 | —(CH₂)₃OCH₃ | naphthyl | 101 |
| 134 | —(CH₂)₃OCH₃ | 3-quinolinyl | 134 |
| 135 | —(CH₂)₃OCH₃ | isoquinolinyl | 176 |
| 136 | —(CH₂)₃OCH₃ | 3-quinolinyl | 174 |
| 137 | —(CH₂)₃OCH₃ | pyrroloquinoline | 167 |

TABLE VI

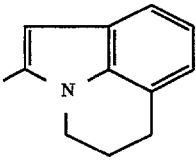

| Example Number | Ar | W | M.p.; °C. |
|---|---|---|---|
| 138 | 1-naphthyl | —CH₂COOCH₃ | 71 |
| 139 | 1-naphthyl | —CH₂COOH | 159 |

TABLE VII

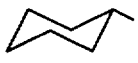

| Example Number | $R_I$ | $R_{II}$ and configuration | $X_1$ | $X_2$ | $X_3$ | W | M.p.; °C. $[\alpha]_D^{20}$ (c=; solvent) |
|---|---|---|---|---|---|---|---|
| 140 | cyclohexyl | —CH₃ (R) | CH₃ | H | OCH₃ | —CH₂COOCH₃ | 130 −87.4 (1; CH₃OH) |
| 141 | cyclohexyl | —CH₃ (R) | CH₃ | H | OCH₃ | —CH₂COOH | 171 −87.3 (1; CH₃OH) |

TABLE VII-continued

Structure: $R_I$-N(-$X_3$,$X_2$,$X_1$,OCH$_3$ substituted phenyl)-CO-CH($R_{II}$)-NH-CO-(indole-2-yl, N-W)

| Example Number | $R_I$ | $R_{II}$ and configuration | $X_1$ | $X_2$ | $X_3$ | W | M.p.; °C. $[\alpha]_D^{20}$ (c=; solvent) |
|---|---|---|---|---|---|---|---|
| 142 | cyclohexyl | —CH$_3$ (R) | CH$_3$ | H | OCH$_3$ | H | 252<br>−81.5<br>(1; CH$_2$Cl$_2$) |
| 143 | —(CH$_2$)$_4$CH$_3$ | —CH$_2$OCH$_2$-phenyl (R) | OCH$_3$ | CH$_3$ | Cl | H | 92<br>−74.4<br>(1.1; CH$_3$OH) |
| 144 | —(CH$_2$)$_4$CH$_3$ | —CH$_2$OCH$_2$-phenyl (R) | OCH$_3$ | CH$_3$ | H | —CH$_2$COOCH$_3$ | 78<br>−88.2<br>(1.4; CH$_3$OH) |
| 145 | —(CH$_2$)$_4$CH$_3$ | —CH$_2$OCH$_2$-phenyl (R) | OCH$_3$ | CH$_3$ | Cl | —CH$_2$COOH | 89<br>−59.3<br>(0.85; CH$_3$OH) |
| 146 | —(CH$_2$)$_4$CH$_3$ | —CH$_2$OCH$_2$-phenyl (R) | OCH$_3$ | CH$_3$ | H | H | 190<br>−104.0<br>(0.75; CH$_3$OH) |
| 147 | —(CH$_2$)$_4$CH$_3$ | —CH$_2$OCH$_2$-phenyl (R) | OCH$_3$ | CH$_3$ | H | —CH$_2$COOH | 72<br>−66.5<br>(1; CH$_3$OH) |
| 148 | cyclooctyl | —CH$_2$OCH$_2$-phenyl (R) | CH$_3$ | H | OCH$_3$ | —CH$_2$COOH | 110<br>−54.0<br>(1.05; CH$_3$OH) |
| 149 | —(CH$_2$)$_4$CH$_3$ | —CH$_2$OCH$_2$-phenyl (R) | OCH$_3$ | CH$_3$ | Cl | —CH$_2$COOCH$_3$ | 55<br>−88.2<br>(1.1; CH$_3$OH) |
| 150 | cyclooctyl | —CH$_2$OCH$_2$-phenyl (R) | CH$_3$ | H | OCH$_3$ | —CH$_2$CO$_2$CH$_3$ | 78<br>−50.0<br>(0.985; CH$_3$OH) |

TABLE VII-continued

| Example Number | $R_I$ | $R_{II}$ and configuration | $X_1$ | $X_2$ | $X_3$ | W | M.p.; °C. $[\alpha]_D^{20}$ (c=; solvent) |
|---|---|---|---|---|---|---|---|
| 151 | —(CH$_2$)$_4$CH$_3$ | —CH$_2$OCH$_2$-C$_6$H$_5$ (R) | CH$_3$ | Cl | H | H | 186 −13.0 (1; DMF) |
| 152 | —(CH$_2$)$_4$CH$_3$ | —CH$_2$OCH$_2$-C$_6$H$_5$ (R) | CH$_3$ | Cl | H | —CH$_2$COOH | 205 −6.0 (1.1; DMF) |
| 153 | —(CH$_2$)$_4$CH$_3$ | —CH$_2$OCH$_2$-C$_6$H$_5$ (R) | CH$_3$ | Cl | H | —CH$_2$COOCH$_3$ | 60 −6.0 (1.125; CH$_3$OH) |
| 154 | cyclohexyl | —CH$_2$OCH$_2$-C$_6$H$_5$ (R) | CH$_3$ | H | OCH$_3$ | —CH$_2$COOCH$_3$ | 80 −45.0 (1.07; CH$_3$OH) |
| 155 | cyclohexyl | —CH$_2$OCH$_2$-C$_6$H$_5$ (R) | CH$_3$ | H | OCH$_3$ | —CH$_2$COOH | 112 −45.0 (1; CH$_3$OH) |
| 156 | cyclohexyl | —CH$_2$OCH$_2$-C$_6$H$_5$ (R) | CH$_3$ | H | OCH$_3$ | H | 185 −70.0 (0.95; DMF) |
| 157 | —CH$_2$CH$_2$-C$_6$H$_5$ | —CH$_2$OCH$_2$-C$_6$H$_5$ (R) | CH$_3$ | H | OCH$_3$ | —CH$_2$COOCH$_3$ | 68 −31.5 (1; CH$_3$OH) |
| 158 | —CH$_2$CH$_2$-C$_6$H$_5$ | —CH$_2$OCH$_2$-C$_6$H$_5$ (R) | CH$_3$ | H | OCH$_3$ | H | 157 −33.0 (1; CH$_3$OH) |

TABLE VII-continued

| Example Number | $R_I$ | $R_{II}$ and configuration | $X_1$ | $X_2$ | $X_3$ | W | M.p.; °C. $[\alpha]_D^{20}$ (c=; solvent) |
|---|---|---|---|---|---|---|---|
| 159 | —(CH$_2$)$_4$CH$_3$ | —CH$_2$OCH$_2$—C$_6$H$_5$ (R) | Cl | CH$_3$ | H | —CH$_2$COOCH$_3$ | 70 −19.0 (1.025; CH$_3$OH) |
| 160 | —CH$_2$CH$_2$—C$_6$H$_5$ | —CH$_2$OCH$_2$—C$_6$H$_5$ (R) | CH$_3$ | H | OCH$_3$ | —CH$_2$COOH | 124 −33.0 (1; CH$_3$OH) |
| 161 | —(CH$_2$)$_4$CH$_3$ | —CH$_2$OCH$_2$—C$_6$H$_5$ (R) | Cl | CH$_3$ | H | —CH$_2$COOH | 135 −19.0 (1.15; CH$_3$OH) |
| 162 | —(CH$_2$)$_4$CH$_3$ | —CH$_2$OCH$_2$—C$_6$H$_5$ (R) | Cl | CH$_3$ | H | H | 186 −14.0 (0.95; CH$_2$Cl$_2$) |
| 163 | —CH$_2$—C$_6$H$_5$ | —CH$_2$OCH$_2$—C$_6$H$_5$ (R) | CH$_3$ | H | OCH$_3$ | —CH$_2$COOCH$_3$ | 73 −80.2 (1; CH$_3$OH) |
| 164 | —(CH$_2$)$_3$CH$_3$ | —CH$_2$OCH$_2$—C$_6$H$_5$ (R) | CH$_3$ | H | OCH$_3$ | —CH$_2$COOCH$_3$ | 60 −35.5 (1; CH$_3$OH) |
| 165 | —CH$_2$—C$_6$H$_5$ | —CH$_2$OCH$_2$—C$_6$H$_5$ (R) | CH$_3$ | H | OCH$_3$ | —CH$_2$COOH | 112 −79.5 (1; CH$_3$OH) |
| 166 | —(CH$_2$)$_4$CH$_3$ | —CH$_2$OCH$_2$—C$_6$H$_5$ (R) | OCH$_3$ | H | OCH$_3$ | —CH$_2$COOCH$_3$ | 58 −58.3 (1; CH$_3$OH) |

TABLE VII-continued

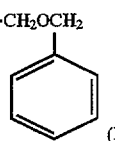

| Example Number | R$_I$ | R$_{II}$ and configuration | X$_1$ | X$_2$ | X$_3$ | W | M.p.; °C. [α]$_D^{20}$ (c=; solvent) |
|---|---|---|---|---|---|---|---|
| 167 | —(CH$_2$)$_4$CH$_3$ | —CH$_2$OC$_6$H$_5$ (R) | OCH$_3$ | H | OCH$_3$ | —CH$_2$COOH | 99 −61.1 (1; CH$_3$OH) |
| 168 | cyclohexyl | —CH$_2$-cyclohexyl (R) | CH$_3$ | H | OCH$_3$ | —CH$_2$COOH | 165 −52.0 (0.805; CH$_3$OH) |
| 169 | —CH$_2$-cyclohexyl | —CH$_2$OC$_6$H$_5$ (R) | CH$_3$ | H | OCH$_3$ | —CH$_2$COOCH$_3$ | 130 −49.0 (0.9; CH$_3$OH) |
| 170 | —CH$_2$-cyclohexyl | —CH$_2$-cyclohexyl (R) | CH$_3$ | H | OCH$_3$ | —CH$_2$COOCH$_3$ | 120 −60.0 (0.97; CH$_3$OH) |
| 171 | —CH$_2$-cyclohexyl | —CH$_2$-cyclohexyl (R) | CH$_3$ | H | OCH$_3$ | —CH$_2$COOH | 165 −55.0 (0.925; CH$_3$OH) |
| 172 | —(CH$_2$)$_3$CH$_3$ | —CH$_2$OC$_6$H$_5$ (R) | CH$_3$ | H | OCH$_3$ | —CH$_2$COOH | 81 −55.1 (1; CH$_3$OH) |
| 173 | —CH$_2$CH$_3$ | —CH$_2$OC$_6$H$_5$ (R) | CH$_3$ | H | OCH$_3$ | —CH$_2$COOCH$_3$ | 71 −59.3 (1; CH$_3$OH) |
| 174 | —CH$_2$CH$_3$ | —CH$_2$OC$_6$H$_5$ (R) | CH$_3$ | H | OCH$_3$ | —CH$_2$COOLi | 100 −63.0 (1; CH$_3$OH) |
| 175 | —CH$_2$-cyclopropyl | —CH$_2$-cyclohexyl (R) | CH$_3$ | H | OCH$_3$ | —CH$_2$COOCH$_3$ | 107 −73.7 (1; CH$_3$OH) |
| 176 | cyclohexyl | —CH$_2$-cyclohexyl (R) | CH$_3$ | H | OCH$_3$ | —CH$_2$COOCH$_3$ | 150 −56.0 (0.925; CH$_3$OH) |

TABLE VII-continued

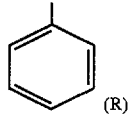

| Example Number | $R_I$ | $R_{II}$ and configuration | $X_1$ | $X_2$ | $X_3$ | W | M.p.; °C. $[\alpha]_D^{20}$ (c=; solvent) |
|---|---|---|---|---|---|---|---|
| 177 | —(CH$_2$)$_4$CH$_3$ | —CH$_2$OCH$_2$-Ph (R) | Cl | OCH$_3$ | H | —CH$_2$COOCH$_3$ | 70<br>−88.2<br>(0.97; CH$_3$OH) |
| 178 | —CH$_2$-cyclopropyl | —CH$_2$-cyclohexyl (R) | CH$_3$ | H | OCH$_3$ | —CH$_2$COOH | 153<br>−78.4<br>(1; CH$_3$OH) |
| 179 | —CH$_2$-cyclopentyl | —CH$_2$OCH$_2$-Ph (R) | CH$_3$ | H | OCH$_3$ | —CH$_2$COOCH$_3$ | 74<br>−53.3<br>(1; CH$_3$OH) |
| 180 | —CH$_3$ | —CH$_2$OCH$_2$-Ph (R) | CH$_3$ | H | OCH$_3$ | —CH$_2$COOCH$_3$ | 64<br>−50.0<br>(1; CH$_3$OH) |
| 181 | —CH$_2$-cyclopentyl | —CH$_2$OCH$_2$-Ph (R) | CH$_3$ | H | OCH$_3$ | —CH$_2$COOH | 110<br>−36.8<br>(1; CH$_3$OH) |
| 182 | —CH$_2$-cyclopropyl | —CH$_2$OCH$_2$-Ph (R) | CH$_3$ | H | OCH$_3$ | —CH$_2$COOH | 126<br>−65.0<br>(1; CH$_3$OH) |
| 183 | CH$_3$ | —CH$_2$OCH$_2$-Ph (R) | CH$_3$ | H | OCH$_3$ | —CH$_2$COOH | 103<br>−58.6<br>(1; CH$_3$OH) |
| 184 | —CH$_2$-cyclopropyl | —CH$_2$OCH$_2$-Ph (R) | CH$_3$ | H | OCH$_3$ | —CH$_2$COOCH$_3$ | 76<br>−57.8<br>(1; CH$_3$OH) |

EXAMPLE 185

Methyl [2-{[butyl(2,6-dimethoxy-4-methylphenyl)carbamoyl]methylcarbamoyl}-1-indolyl]acetate.

(I): Ar = 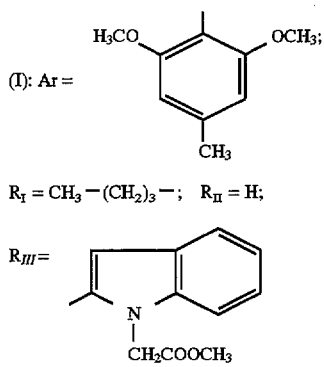

$R_I = CH_3-(CH_2)_3-$;  $R_{II} = H$;

$R_{III} =$

This product is prepared according to the process described in EXAMPLE 1 from [butyl(2,6-dimethoxy-4-methylphenyl)carbamoyl]methylamine and 1-(methoxycarbonylmethyl)-2-indolecarboxylic acid; M.p.= 139° C.; Yield: 90%.

EXAMPLE 186

(I): Ar = 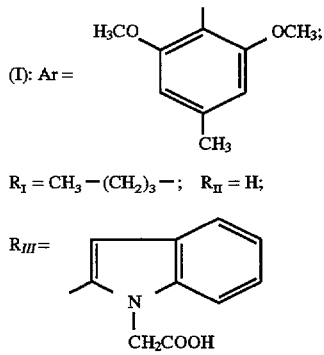

$R_I = CH_3-(CH_2)_3-$;  $R_{II} = H$;

$R_{III} =$

By carrying out the preparation according to EXAMPLE 2, from methyl{2-[[butyl(2,6-dimethoxy-4-methylphenyl)carbamoyl]methylcarbamoyl]-1-indolyl}acetate (EXAMPLE 185), {2-[[butyl(2,6-dimethoxy-4-methylphenyl)carbamoyl]methylcarbamoyl]-1-indolyl}acetic acid is prepared; M.p.=211° C.; Yield: 92%.

EXAMPLE 187

(I): Ar = 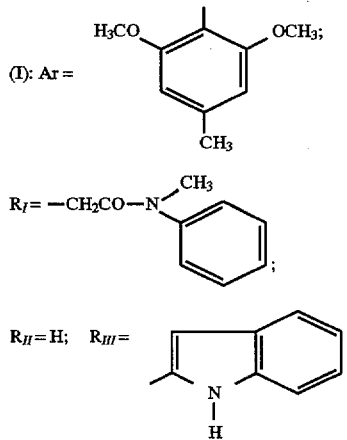

$R_I = -CH_2CO-N$ $R_{II} = H$;  $R_{III} =$

By carrying out the preparation according to EXAMPLE 3, N-{[((methylphenylcarbamoyl)methyl)(2,6-dimethoxy-4-methylphenyl)carbamoyl]methyl}-1H-indole-2-carboxamide is prepared, M.p.=116° C.; Yield: 90%.

EXAMPLE 188

(I): Ar = 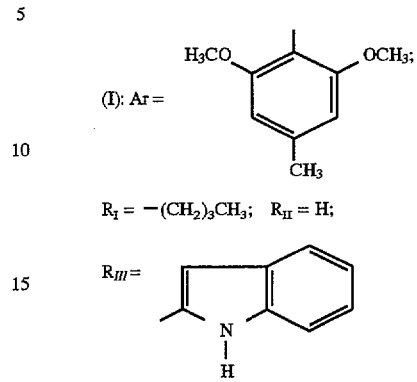

$R_I = -(CH_2)_3CH_3$;  $R_{II} = H$;

$R_{III} =$

By carrying out the preparation according to EXAMPLE 3, N-[[butyl(2,6-dimethoxy-4-methylphenyl)carbamoyl]methyl]-1H-indole-2-carboxamide is prepared; M.p.=210° C.; Yield: 91%.

EXAMPLE 189

(I): Ar = 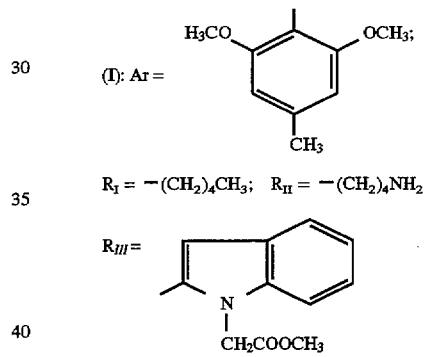

$R_I = -(CH_2)_4CH_3$;  $R_{II} = -(CH_2)_4NH_2$ $R_{III} =$ 5.6 g of methyl (R)-{2-[N-{1-[(2,6-dimethoxy-4-methylphenyl)pentylcarbamoyl]-5-(benzyloxycarbonylamino)pentyl}carbamoyl]indol-1-yl}acetate (EXAMPLE 66) are dissolved in 170 ml of methanol and 0.56 g of 10% Pd/C is added thereto. Hydrogenation is carried out under a pressure of 3 bar and the reaction mixture is left at 30° C., while maintaining this pressure, for 18 hours. After cooling, the catalyst is filtered over a bed of celite and evaporation is carried out to dryness. The residual oil is purified by flash chromatography on silica gel, eluent: $CH_2Cl_2/CH_3OH/AcOH$ 90/10/0.5 (v/v/v) in order to obtain white crystals of methyl (R)-{2-[N-{1-[(2,6-dimethoxy-4-methylphenyl)pentylcarbamoyl]-5-aminopentyl}carbamoyl]indol-1-yl}acetate, M.p.=78° C., $[\alpha]_D^{20}=-47.6°$ (c=1, $CH_3OH$), Yield: 85%.

EXAMPLE 190

(I): Ar = 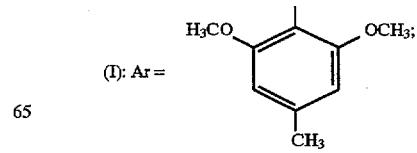

$R_I$ = —(CH$_2$)$_4$CH$_3$; $R_{II}$ = —(CH$_2$)$_4$NH$_2$ $R_{III}$ = 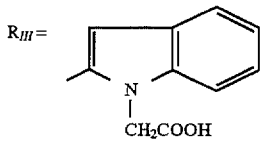

0.7 g of the compound prepared in EXAMPLE 189 above is dissolved in 20 ml of methanol and 0.075 g of lithium hydroxide hydrate is added and the reaction mixture is left at room temperature for 18 hours. Evaporation is carried out to dryness and the residue is taken up in water. The aqueous phase is acidified with 1N HCl and extraction is carried out with ethyl acetate. The organic extracts are dried over anhydrous sodium sulphate and evaporated to dryness. The crystals obtained are purified by flash chromatography on silica gel, eluent: CH$_2$Cl$_2$/CH$_3$OH, 9/1 (v/v) in order to obtain white crystals of (R)-{2-[N-{1-[(2,6-dimethoxy-4-methylphenyl)pentylcarbamoyl]-5-aminopentyl}carbamoyl]indol-1-yl}acetic acid, M.p.=173° C., $[\alpha]_D^{20}$=−173.0° (c=0.6, CH$_3$OH). Yield: 87%.

EXAMPLE 191

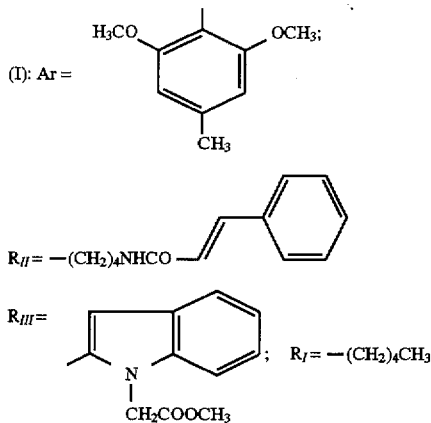

0.87 g of methyl (R)-{2-[N-{1-[(2,6-dimethoxy-4-methylphenyl)pentylcarbamoyl]-5-aminopentyl}carbamoyl]indol-1-yl}acetate, 0.645 g of BOP and 0.23 g of cinnamic acid are successively added to 30 ml of dimethylformamide. After cooling to −5° C., 0.26 g of N-ethylmorpholine is added under an inert atmosphere and the reaction mixture is maintained at 0° C. for 2 hours and is then left at room temperature for 18 hours. The reaction mixture is poured into a large volume of water and extraction is carried out with ethyl acetate. The organic extracts are dried over anhydrous sodium sulphate and evaporated to dryness. The residual oil is purified by flash chromatography on silica gel, eluent: CH$_2$Cl$_2$/CH$_3$OH 97/3 (v/v) in order to obtain methyl (R)-{2-[N-{1-[(2,6-dimethoxy-4-methylphenyl)pentylcarbamoyl]-5-(cinnamoylamino)pentyl}carbamoyl]indol-1-yl}acetate in the form of an oil.

EXAMPLE 192

(I): Ar = 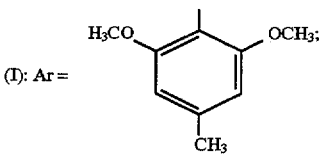

$R_{II}$ = —(CH$_2$)$_4$NHCO— 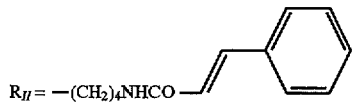

$R_{III}$ = 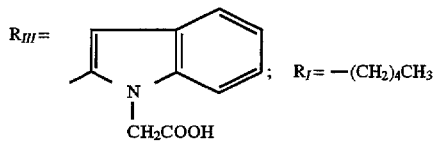 ; $R_I$ = —(CH$_2$)$_4$CH$_3$

The preceding ester is saponified with LiOH.H$_2$O/CH$_3$OH, as previously, in order to provide white crystals of (R)-{2-[N-{1-[(2,6-dimethoxy-4-methylphenyl)pentylcarbamoyl]-5-(cinnamoylamino)pentyl}carbamoyl]indol-1-yl}acetic acid, M.p.=172° C., $[\alpha]_D^{20}$=−21.2° (c=0.8, CH$_3$OH).

We claim:
1. Compound of formula:

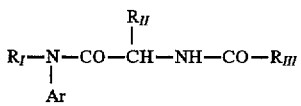

in which $R_I$ represents a (C$_3$–C$_8$) alkyl; an arylalkyl -Alk-Ar$_1$, where Alk represents an alkylene containing 1 to 4 carbon atoms and Ar$_1$ represents a phenyl group or a heterocycle optionally substituted by a halogen, a (C$_1$–C$_3$) alkyl, a (C$_1$–C$_3$) alkoxy, a trifluoromethyl or a hydroxyl; a cycloalkylalkyl in which the alkyl is (C$_1$–C$_4$) and the cycloalkyl is (C$_3$–C$_{10}$); a (C$_3$–C$_{10}$) cycloalkyl optionally substituted by a hydroxyl, a (C$_1$–C$_3$) alkoxy or a (C$_1$–C$_3$) alkyl, it being possible for the said alkyl to substitute the same carbon atom twice; an alkoxyalkyl in which the alkoxy is (C$_1$–C$_4$) and the alkyl is (C$_2$–C$_5$); or a group (AB)N—CO—(CH$_2$)$_r$—, where A is a (C$_1$–C$_3$) alkyl, B is a (C$_1$–C$_3$) alkyl or a phenyl or else A and B form, with the nitrogen atom to which they are bonded, a heterocycle chosen from pyrrolidine, piperidine and morpholine, and R is 1, 2 or 3;

$R_{II}$ represents hydrogen; a (C$_1$–C$_6$) alkyl; a (C$_1$–C$_5$) hydroxyalkyl; a group —(CH$_2$)$_m$—COR$_2$ in which m is an integer from 1 to 3 and R$_2$ represents a hydroxyl, a (C$_1$–C$_4$) alkoxy group, a benzyloxy group or a group —NR$_3$R$_4$ in which R$_3$ or R$_4$ independently represent hydrogen, a (C$_1$–C$_4$) alkyl or constitute, with the nitrogen atom to which they are bonded, a heterocycle chosen from pyrrolidine, piperidine and morpholine; an aralkyl group —(CH$_2$)$_n$—Ar$_2$ in which n is equal to 0 or represents an integer from 1 to 4 and Ar$_r$ represents a phenyl or a heterocycle optionally substituted by a halogen, a (C$_1$–C$_3$) alkyl, a (C$_1$–C$_3$) alkoxy, a trifluoromethyl, a hydroxyl or a benzyloxy; a cycloalkylalkyl in which the alkyl is (C$_1$–C$_4$) and the cycloalkyl is (C$_3$–C$_{10}$); a (C$_1$–C$_4$) aminoalkyl; a group R—CO—NH—(CH$_2$)$_x$— in which x represents an integer from 1 to 4 and R represents a $(C_1-C_4)$ alkyl, a phenyl, a benzyl, a 2-phenylethenyl or a benzyloxy, the aromatic rings optionally being substituted by a halogen, a $(C_1-C_3)$ alkyl, a $(C_1-C_3)$ alkoxy, a trifluoromethyl, a hydroxyl or a sulpho or carboxyl group; a guanidino$(C_1-C_4)$alkyl; an imidazolyl $(C_1-C_3)$ alkyl; an alkylthioalkyl in which the alkyls are $(C_1-C_3)$; an aralkylthioalkyl in which the aryl part is optionally heterocyclic and the alkyl parts are $(C_1-C_3)$, the aryl optionally being substituted by a halogen, a $(C_1-C_3)$ alkyl, a $(C_1-C_3)$ alkoxy, a trifluoromethyl or a hydroxyl; a benzyloxyalkyl in which the alkyl is $(C_1-C_3)$ and the phenyl is optionally substituted by a halogen, a hydroxyl, a $(C_1-C_3)$ alkoxy, a $(C_1-C_3)$ alkyl, a trifluoromethyl, a nitrile or a nitro;

$R_{III}$ represents an indolyl group which is unsubstituted, substituted on a carbon or substituted on the nitrogen by a $(C_1-C_3)$ alkyl or $(C_1-C_4)$ alkylcarbonyl group, by a group $-(CH_2)_p-COR_5$, p being an integer from 0 to 4 and $R_5$ representing $OR'_5$ or $NR'_5R''_5$ with $R'_5$ and $R''_5$, which may or may not be identical, representing hydrogen or a $(C_1-C_4)$ alkyl or else $R'_5$ and $R''_5$ form, together with the nitrogen atom to which they are bonded, a piperidine, by a $(C_1-C_4)$ hydroxyalkyl, by a $(C_2-C_6)$ alkoxyalkyl, by a $(C_2-C_4)$ cyanoalkyl, by a tetrahydropyranyl, by a $(C_1-C_4)$ adamantylaminocarbonylalkyl or by a chain $-(CH_2)_q-$, q being an integer from 2 to 4, one of the carbons of which substitutes the phenyl ring of the indole group in order to constitute a ring;

Ar represents 2-methoxyphenyl group containing at least two other substituents chosen from a $(C_1-C_3)$ alkyl, a $(C_1-C_3)$ alkoxy, a halogen atom and a trifluoromethyl; or Ar represents a naphthyl group;

or optionally one of their salts.

2. Compound according to claim 1, of formula:

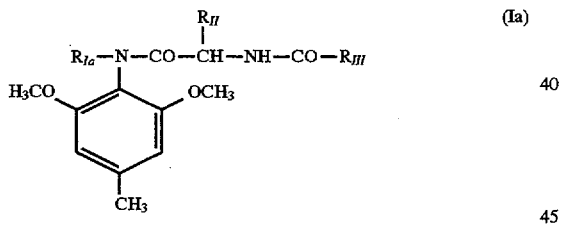

in which $R_{II}$ and $R_{III}$ are as defined in claim 1 for (I) and $R_{Ia}$ represents a $(C_5-C_8)$ alkyl; an arylalkyl -Alk-Ar$_1$, where Alk represents an alkylene containing 1 to 4 carbon atoms and Ar$_1$ represents a phenyl group or a heterocycle optionally substituted by a halogen, a $(C_1-C_3)$ alkyl, a $(C_1-C_3)$ alkoxy, a trifluoromethyl or a hydroxyl; a cycloalkylalkyl in which the alkyl is $(C_1-C_4)$ and the cycloalkyl is $(C_3-C_{10})$; a $(C_3-C_{10})$ cycloalkyl which is optionally substituted by a hydroxyl, a $(C_1-C_3)$ alkoxy, or a $(C_1-C_3)$ alkyl, it being possible for the said alkyl to substitute the same carbon atom twice; an alkoxyalkyl in which the alkoxy is $(C_1-C_4)$ and the alkyl is $(C_2-C_5)$; or a group (AB)N—CO—$(CH_2)_r$—, where A is a $(C_1-C_3)$ alkyl, B is a $(C_1-C_3)$ alkyl or a phenyl or else A and B form, with the nitrogen atom to which they are bonded, a heterocycle chosen from pyrrolidine, piperidine and morpholine, and r is 1, 2 or 3; or a salt thereof.

3. Compound according to claim 1 of formula (I) in which Ar represents a naphthyl group and $R_I$ represents a $(C_5-C_8)$ alkyl; an arylalkyl -Alk-Ar$_1$, where Alk represents an alkylene containing 1 to 4 carbon atoms and Ar$_1$ represents a phenyl group or a heterocycle optionally substituted by a halogen, a $(C_1-C_3)$ alkyl, a $(C_1-C_3)$ alkoxy, a trifluoromethyl or a hydroxyl; a cycloalkylalkyl in which the alkyl is $(C_1-C_4)$ and the cycloalkyl is $(C_3-C_{10})$; a $(C_3-C_{10})$ cycloalkyl which is optionally substituted by a hydroxyl, a $(C_1-C_3)$ alkoxy, or a $(C_1-C_3)$ alkyl, it being possible for the said alkyl to substitute the same carbon atom twice; an alkoxyalkyl in which the alkoxy is $(C_1-C_4)$ and the alkyl is $(C_2-C_5)$; or a group (AB)N—CO—$(CH_2)_r$—, where A is a $(C_1-C_3)$ alkyl, B is a $(C_1-C_3)$ alkyl or a phenyl or else A and B form, with the nitrogen atom to which they are bonded, a heterocycle chosen from pyrrolidine, piperidine and morpholine, and r is 1, 2 or 3; or a salt thereof.

4. Compound according to claim 1, of formula (I) in which $R_{II}$, is other than hydrogen and in which the carbon carrying the substituent $R_{II}$ is in the R configuration or a salt thereof.

5. Pharmaceutical composition containing, as active principle, a compound according to claim 1 in combination with a pharmaceutically acceptable vehicle.

6. Pharmaceutical composition according to claim 5, in unit dosage form, in which the pharmaceutically acceptable vehicle is at least one pharmaceutical excipient.

7. Pharmaceutical composition according to claim 6, containing from 0.5 to 1,000 mg of the active principle.

8. Compound of formula:

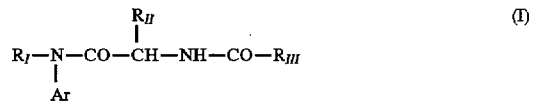

in which $R_I$ represents a $(C_3-C_8)$ alkyl; an arylalkyl -Alk-Ar$_1$, where Alk represents an alkylene containing 1 to 4 carbon atoms and Ar$_1$ represents a phenyl group or a heterocycle optionally substituted by a halogen, a $(C_1-C_3)$ alkyl, a $(C_1-C_3)$ alkoxy, a trifluoromethyl or a hydroxyl; a cycloalkylalkyl in which the alkyl is $(C_1-C_4)$ and the cycloalkyl is $(C_3-C_{10})$; a $(C_3-C_{10})$ cycloalkyl optionally substituted by a hydroxyl, a $(C_1-C_3)$ alkoxy or a $(C_1-C_3)$ alkyl, it being possible for the said alkyl to substitute the same carbon atom twice; an alkoxyalkyl in which the alkoxy is $(C_1-C_4)$ and the alkyl is $(C_2-C_5)$;

$R_{II}$ represents hydrogen; a $(C_1-C_6)$ alkyl; a $(C_1-C_5)$ hydroxyalkyl; an aralkyl group —$(CH_2)_n$—Ar$_2$ in which n is equal to 0 or represents an integer from 1 to 4 and Ar$_2$ represents a heterocycle optionally substituted by a halogen, a $(C_1-C_3)$ alkyl, a $(C_1-C_3)$ alkoxy, a trifluoromethyl, a hydroxyl or a benzyloxy; a cycloalkylalkyl in which the alkyl is $(C_1-C_4)$ and the cycloalkyl is $(C_3-C_{10})$; a $(C_1-C_4)$ aminoalkyl; a group R—CO—NH—$(CH_2)_x$— in which x represents an integer from 1 to 4 and R represents a $(C_1-C_4)$ alkyl, a phenyl, a benzyl, a 2-phenylethenyl or a benzyloxy, the aromatic rings optionally being substituted by a halogen, a $(C_1-C_3)$ alkyl, a $(C_1-C_3)$ alkoxy, a trifluoromethyl, a hydroxyl or a sulpho or carboxyl group; a guanidino$(C_1-C_4)$alkyl; an imidazolyl $(C_1-C_3)$ alkyl; an alkylthioalkyl in which the alkyls are $(C_1-C_3)$; an aralkylthioalkyl in which the aryl part is optionally heterocyclic and the alkyl parts are $(C_1-C_3)$, the aryl optionally being substituted by a halogen, a $(C_1-C_3)$ alkyl, a $(C_1-C_3)$ alkoxy, a trifluoromethyl or a hydroxyl; a benzyloxyalkyl in which the alkyl is $(C_1-C_3$ and the phenyl is optionally substituted by a halogen, a hydroxyl, a $(C_1-C_3)$ alkoxy, a $(C_1-C_3)$ alkyl, a trifluoromethyl, a nitrile or a nitro;

$R_{III}$ represents an indolyl group which is unsubstituted, substituted on a carbon or substituted on the nitrogen by a ($C_1$–$C_3$) alkyl or ($C_1$–$C_4$) alkylcarbonyl group, by a group —($CH_2$)$_p$—$COR_5$, p being an integer from 0 to 4 and $R_5$ representing $OR'_5$ or $NR'_5R''_5$ with $R'_5$ and $R''_5$, which may or may not be identical, representing hydrogen or a ($C_1$–$C_4$) alkyl or else $R'_5$ and $R''_5$ form, together with the nitrogen atom to which they are bonded, a piperidine, by a ($C_1$–$C_4$) hydroxyalkyl, by a ($C_2$–$C_6$) alkoxyalkyl, by a ($C_2$–$C_4$) cyanoalkyl, by a tetrahydropyranyl, by a ($C_1$–$C_4$) adamantylaminocarbonylalkyl or by a chain —($CH_2$)$_q$—, q being an integer from 2 to 4, one of the carbons of which substitutes the phenyl ring of the indole group in order to constitute a ring;

Ar represents 2-methoxyphenyl group containing at least two other substituents chosen from a ($C_1$–$C_3$) alkyl, a ($C_1$–$C_3$) alkoxy, a halogen atom and a trifluoromethyl; or Ar represents a naphthyl group;

or a salt thereof.

9. Compound of formula:

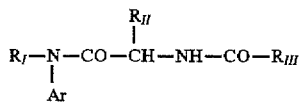  (I)

in which $R_I$ represents a ($C_3$–$C_8$) alkyl; an arylalkyl -Alk-$Ar_1$, where Alk represents an alkylene containing 1 to 4 carbon atoms and $Ar_1$ represents a phenyl group or a heterocycle optionally substituted by a halogen, a ($C_1$–$C_3$) alkyl, a ($C_1$–$C_3$) alkoxy, a trifluoromethyl or a hydroxyl; a cycloalkylalkyl in which the alkyl is ($C_1$–$C_4$) and the cycloalkyl is ($C_3$–$C_{10}$); a ($C_3$–$C_{10}$) cycloalkyl optionally substituted by a hydroxyl, a ($C_1$–$C_3$) alkoxy or a ($C_1$–$C_3$) alkyl, it being possible for the said alkyl to substitute the same carbon atom twice; or an alkoxyalkyl in which the alkoxy is ($C_1$–$C_4$) and the alkyl is ($C_2$–$C_5$);

$R_{II}$ represents hydrogen; a ($C_1$–$C_6$) alkyl; a ($C_1$–$C_5$) hydroxylalkyl; a cycloalkylalkyl in which the alkyl is ($C_1$–$C_4$) and the cycloalkyl is ($C_3$–$C_{10}$); a ($C_1$–$C_4$) aminoalkyl; a group R—CO—NH—($CH_2$)$_x$— in which x represents an integer from 1 to 4 and R represents a ($C_1$–$C_4$) alkyl, a phenyl, a benzyl, a 2-phenylethenyl or a benzyloxy, the aromatic rings optionally being substituted by a halogen, a ($C_1$–$C_3$) alkyl, a ($C_1$–$C_3$) alkoxy, a trifluoromethyl, a hydroxyl or a sulpho or carboxyl group; a guanidino($C_1$–$C_4$) alkyl; an imidazolyl ($C_1$–$C_3$) alkyl; an alkylthioakyl in which the alkyls are ($C_1$–$C_3$); an aralkylthioalkyl in which the aryl part is optionally heterocyclic and the alkyl parts are ($C_1$–$C_3$), the aryl optionally being substituted by a halogen, a ($C_1$–$C_3$) alkyl, a ($C_1$–$C_3$) alkoxy, a trifluoromethyl or a hydroxyl; a benzyloxyalkyl in which the alkyl is ($C_1$–$C_3$) and the phenyl is optionally substituted by a halogen, a hydroxyl, a ($C_1$–$C_3$) alkoxy, a ($C_1$–$C_3$) alkyl, a trifluoromethyl, a nitrile or a nitro;

$R_{III}$ represents an indolyl group which is unsubstituted, substituted on a carbon or substituted on the nitrogen by a ($C_1$–$C_3$) alkyl or ($C_1$–$C_4$) alkylcarbonyl group, by a group —($CH_2$)$_p$—$COR_5$, p being an integer from 0 to 4 and $R_5$ representing $OR'_5$ or $N'_5RR''_5$ with $R'_5$ and $R''_5$, which may or may not be identical, representing hydrogen or a ($C_1$–$C_4$) alkyl or else $R'_5$ and $R''_5$ form, together with the nitrogen atom to which they are bonded, a piperidine, by a ($C_1$–$C_4$) hydroxyalkyl, by a ($C_2$–$C_6$) alkoxyalkyl, by a ($C_2$–$C_4$) cyanoalkyl, by a tetrahydropyranyl, by a ($C_1$–$C_4$) adamantylaminocarbonylalkyl or by a chain —($CH_2$)$_q$—, q being an integer from 2 to 4, one of the carbons of which substitutes the phenyl ring of the indole group in order to constitute a ring;

Ar represents 2-methoxyphenyl group containing at least two other substitutents chosen from ($C_1$–$C_3$) alkyl, a ($C_1$–$C_3$) alkoxy, a halogen atom and a trifluoromethyl; or Ar represents a naphthyl group;

or a salt thereof.

10. Process for the preparation of a compound according to claim 1 of formula (I), characterized in that an amine of formula:

  (II)

in which Ar and $R_I$ are as defined above, is treated with an N-protected amino acid of formula:

  (III)

in which $R_{II}$ is as defined for (I) and in which, if appropriate, the reactive groups of $R_{II}$ have been protected, in order to lead to a compound of formula:

  (IV)

in which $R_I$, Ar and $R_{II}$ are as defined above, which, after conversion, leads to a compound (I) according to claim 1 or one of its optional salts.

* * * * *